US012779144B2

(12) United States Patent
Zhang et al.

(10) Patent No.: US 12,779,144 B2
(45) Date of Patent: Nov. 3, 2026

(54) INTRANASAL DELIVERY DEVICE FOR DELIVERING A MEDICATION SOLUTION

(71) Applicant: Amphastar Pharmaceuticals, Inc., Rancho Cucamonga, CA (US)

(72) Inventors: Jack Y. Zhang, Diamond Bar, CA (US); Mary Z. Luo, Diamond Bar, CA (US); Rong Zhou, Brea, CA (US); Anthony D. Marrs, Costa Mesa, CA (US); Lameng Lei, Rancho Cucamonga, CA (US); Yi Xia, Oak Hills, CA (US); Steven K. Johnson, Rancho Cucamonga, CA (US); Shih Wing Yip, Chino Hills, CA (US); Fonda Su, Hacienda Heights, CA (US); Ronggen Wan, Chino Hills, CA (US)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 698 days.

(21) Appl. No.: 18/183,667

(22) Filed: Mar. 14, 2023

(65) Prior Publication Data

US 2024/0307637 A1 Sep. 19, 2024

(51) Int. Cl.
*A61M 11/06* (2006.01)
*A61M 11/00* (2006.01)
(Continued)

(52) U.S. Cl.
CPC ........... *A61M 11/06* (2013.01); *A61M 11/007* (2014.02); *A61M 15/0036* (2014.02);
(Continued)

(58) Field of Classification Search
CPC ................ A61M 11/007; A61M 11/06; A61M 15/0065; A61M 15/0086; A61M 15/08;
(Continued)

(56) References Cited

U.S. PATENT DOCUMENTS 5,307,953 A * 5/1994 Regan ...................... B05B 11/02 604/203
5,383,850 A * 1/1995 Schwab ............ A61M 15/0065 128/203.15
(Continued)

FOREIGN PATENT DOCUMENTS

DE 19837127 A1 * 5/1999 ............. B05B 11/02
DE 19905993 A1 * 8/2000 ......... B05B 11/1091
(Continued)

OTHER PUBLICATIONS

English translation for FR 2684304, machine translated by espacenet.com.*
(Continued)

*Primary Examiner* — Tu A Vo
(74) *Attorney, Agent, or Firm* — IceMiller LLP

(57) ABSTRACT

An intranasal (IN) delivery gas-phase impermeable device for delivery between 0.2 mL and 1.0 mL of a medication solution includes an injector barrel including a plurality of slit openings disposed circumferentially along the injector barrel, a center guide positioned lengthwise within the injector barrel, a cannula in fluid communication with the medication solution fixed in position by the center guide, and a vial configured to couple with the injector barrel. The vial includes a pliable rubber stopper with multiple seal rings, each seal ring having a geometry configured to form a gas-phase impermeable seal with an internal surface of the vial. The cannula bisects the pliable rubber stopper. The device includes a base configured to reversibly engage with one or more of the slit openings of the injector barrel during actuation of the device, which may involve compression of the base toward the injector barrel.

21 Claims, 15 Drawing Sheets

(51) Int. Cl.
*A61M 15/00* (2006.01)
*A61M 15/08* (2006.01)

(52) U.S. Cl.
CPC ...... *A61M 15/004* (2014.02); *A61M 15/0065* (2013.01); *A61M 15/0086* (2013.01); *A61M 15/08* (2013.01); *A61M 2205/581* (2013.01); *A61M 2205/582* (2013.01); *A61M 2205/584* (2013.01)

(58) Field of Classification Search
CPC ............ A61M 15/0036; A61M 15/004; B05B 11/02–029; A61K 38/00; A61K 31/122; A61K 31/21; A61K 31/407; A61K 31/485; A61K 31/4985; A61K 31/519; A61K 9/0043
See application file for complete search history.

(56) References Cited

U.S. PATENT DOCUMENTS 6,398,074 B1* 6/2002 Bruna .................. B05B 11/062 222/386
6,626,379 B1* 9/2003 Ritsche .............. B05B 11/0078 239/303
6,708,846 B1* 3/2004 Fuchs ................ B05B 11/1091 222/386
6,997,357 B2* 2/2006 Fuchs ................ B05B 11/0083 222/145.5
7,044,125 B2 5/2006 Vedrine et al.
7,708,719 B2 5/2010 Wilmot et al.
7,967,010 B2 6/2011 Vedrine et al.
8,016,795 B2 9/2011 Barrelle et al.
8,627,816 B2 1/2014 Edwards et al.
9,480,804 B2 11/2016 Vedrine et al.
9,517,307 B2 12/2016 Blondino et al.
9,542,826 B2 1/2017 Edwards et al.
10,751,739 B2* 8/2020 Petit .................... A61M 15/004
2002/0117513 A1* 8/2002 Helmlinger ....... A61M 15/0036 222/321.6
2007/0051362 A1 3/2007 Sullivan et al.
2010/0095957 A1* 4/2010 Corbacho ......... A61M 15/0028 128/200.14
2013/0102596 A1 4/2013 Sun
2013/0298902 A1* 11/2013 Denton .................. A61M 11/06 128/200.14
2014/0060523 A1* 3/2014 Sogaro .................. A61M 15/08 128/200.14
2015/0258287 A1 9/2015 Shahaf et al.
2016/0008277 A1 1/2016 Crystal et al.
2016/0243313 A1* 8/2016 Tran .................. A61M 5/31548
2018/0361085 A1* 12/2018 Malhotra .......... A61M 15/0036
2020/0009333 A1* 1/2020 Dunne .................... B05B 15/33
2020/0171252 A1* 6/2020 Greiner-Perth ....... B05B 1/3452
2020/0197630 A1 6/2020 Petit
2021/0361884 A1* 11/2021 Fröhlich .............. A61M 11/001
2021/0369992 A1* 12/2021 Norrant ................. A61M 15/08
2022/0249787 A1* 8/2022 Kamishita ......... A61M 15/0028
2023/0270953 A1* 8/2023 Hubert ................. A61M 11/007 128/200.14
2025/0177667 A1* 6/2025 Gibbons ............... A61M 15/08

FOREIGN PATENT DOCUMENTS

FR 2684304 A1* 5/1993 .......... A61M 15/004
WO WO2002083230 A1 10/2002
WO WO2022049087 A1 3/2022

OTHER PUBLICATIONS

International Search Report & Written Opinion issued in PCT/US2024/015933, mailed May 21, 2024 [11 pages].

* cited by examiner

Rib Thickness (Unit: mm)

| | Sample # | Top Rib | | | Middle Ring | | | Bottom Rib | | |
|---|---|---|---|---|---|---|---|---|---|---|
| | | Location 1 | Location 2 | Sub-Ave | Location 1 | Location 2 | Sub-Ave | Location 1 | Location 2 | Sub-Ave |
| Delivery Device | 1 | 1.670 | 1.658 | 1.664 | 1.199 | 1.148 | 1.173 | 1.385 | 1.398 | 1.392 |
| | 2 | 1.815 | 1.853 | 1.834 | 1.202 | 1.228 | 1.215 | 1.436 | 1.513 | 1.474 |
| | 3 | 1.557 | 1.646 | 1.601 | 1.139 | 1.111 | 1.125 | 1.122 | 1.394 | 1.258 |
| | 4 | 1.713 | 1.823 | 1.768 | 1.167 | 1.120 | 1.144 | 1.369 | 1.385 | 1.377 |
| | 5 | 1.845 | 1.904 | 1.875 | 1.127 | 1.146 | 1.136 | 1.260 | 1.302 | 1.281 |
| | **Average** | | | **1.748** | | | **1.159** | | | **1.356** |
| | **Stdev** | | | **0.114** | | | **0.036** | | | **0.088** |
| Aptar (R) Unidose System | 1 | 0.370 | 0.392 | 0.381 | 0.408 | 0.394 | 0.401 | 0.406 | 0.394 | 0.400 |
| | 2 | 0.383 | 0.395 | 0.389 | 0.392 | 0.402 | 0.397 | 0.418 | 0.406 | 0.412 |
| | 3 | 0.387 | 0.380 | 0.384 | 0.395 | 0.387 | 0.391 | 0.402 | 0.418 | 0.410 |
| | 4 | 0.355 | 0.364 | 0.360 | 0.364 | 0.355 | 0.360 | 0.383 | 0.392 | 0.388 |
| | 5 | 0.350 | 0.330 | 0.340 | 0.350 | 0.350 | 0.350 | 0.364 | 0.370 | 0.367 |
| | **Average** | | | **0.371** | | | **0.380** | | | **0.395** |
| | **Stdev** | | | **0.021** | | | **0.023** | | | **0.018** |

*FIG. 17*

INTRANASAL DELIVERY DEVICE FOR DELIVERING A MEDICATION SOLUTION

TECHNICAL FIELD

The present disclosure relates to an intranasal (IN) delivery device for delivering a medication solution. More specifically, the present disclosure relates to an IN gas-phase impermeable delivery device for delivering a non-sterile or sterile, relatively large volume (between 0.2 mL and 1 mL) of medication solution.

BACKGROUND

IN spray devices can be used to administer medication solutions to treat a variety of medical conditions, such as allergies and sinusitis. Administering such medication solutions via the IN device may be preferred by patients or emergency care providers over administering medications with a needle and/or syringe, such as intramuscular (IM) injection. This may be desirable, since many patients may have a fear of needles or do not want to experience the pain associated with needle and/or syringe injections. Accordingly, IN spray devices may be used to intranasally administer medications that are currently administered via needle and/or syringe. As there is interest in administering medications without the use of a needle and/or syringe, improved IN spray devices are needed. Such desirable improvements can include or consider effectively sealing medication solution contained within a vial of the IN spray device and capable of delivering sterile medication or oxygen-sensitive medication in a stable manner and in quantity greater than the current IN spray device.

Current IN spray devices are configured to deliver smaller amounts of medication solutions, such as amounts of about 0.1 mL or less. Further many known IN delivery devices are incapable of effectively sealing the medication solution off from air or the environment, thus allowing gaseous-phase substances, such as oxygen gas, to come into contact with the medication solution. Such contact between gaseous-phase substance, such as oxygen gas, is undesirable as this can contaminate or degrade the medication solution. As such, there is a need for improved IN spray devices.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter.

In embodiments, provided is an IN delivery gas-phase impermeable device for delivery between 0.2 mL and 1.0 mL of a medication solution. The intranasal delivery gas-phase impermeable device includes an injector barrel, a vial, and a base. The injector barrel includes a cylindrical tube having a plurality of slit openings disposed circumferentially along a bottom of an external tube of the injector barrel. The injector barrel includes an inner cylindrical tube inside the external tube, the inner cylindrical tube extending lengthwise from an upper portion toward the plurality of slit openings of the injector barrel. The injector barrel includes a centering guide positioned lengthwise within the injector barrel, and a cannula in fluid communication with the medication solution and secured in position by the centering guide. The vial is configured to couple with the injector barrel. The vial includes a pliable rubber stopper including a plurality of seal rings, each seal ring having a geometry configured to form a gas-phase impermeable seal with an internal surface of the vial. The cannula bisects the pliable rubber stopper. The base is configured to reversibly engage with one or more of the slit openings of the injector barrel during actuation of the intranasal delivery gas-phase impermeable device.

In embodiments of the IN delivery gas-phase impermeable device the external tube, the inner tube, the centering guide, and the cannula of the injector barrel are homocentric.

In embodiments, the injector barrel further includes a tip configured to deliver medication into a nostril of a patient and further configured to form an interference-type fit within a circumference of the nostril of the patient, wherein a length of the tip is not more than 25 mm.

In embodiments, a diameter of the external tube of the injector barrel is larger than a nostril of a patient.

In embodiments, the external tube of the injector barrel further includes a pair of finger flanges extending laterally away from the injector barrel, each finger flange positioned diametrically opposite to each other, and wherein each finger flange is configured to support a user's finger.

In embodiments, the cylindrical tube includes a plurality of ribs, wherein each rib is disposed lengthwise on its inner surface, wherein the plurality of ribs are configured to (i) guide the base in a fixed clockwise or counterclockwise position within the injector barrel and (ii) hold the vial in a radially fixed position.

In embodiments, the vial is made from glass or plastic, and the vial is configured as a cylinder-shaped vial with a flat bottom, a cylinder-shaped tube with a non-flat bottom, or a cartridge tube.

In embodiments, the medication solution is a sterile medication solution or a non-sterile medication solution.

In embodiments, the vial is configured to store the medication solution between the pliable rubber stopper and a bottom section of the vial.

In embodiments, the medication solution comprises a true solution, a suspension, or an emulsion.

In embodiments, the medication solution includes one or more active pharmaceutical ingredients (APIs) selected from epinephrine ($C_9H_{13}NO_3$), ketorolac ($C_{15}H_{13}NO_3$), naloxone ($C_{19}H_{21}NO_4$), midazolam ($C_{18}H_{13}ClFN_3$), sildenafil ($C_{22}H_{30}N_6O_4S$), tadalafil ($C_{22}H_{19}N_3O_4$), phytonadione ($C_{31}H_{46}O_2$), insulin aspart ($C_{256}H_{381}N_{65}O_{79}S_6$), nitroglycerin ($C_3H_5N_3O_9$), teriparatide ($C_{181}H_{291}N_{55}O_{51}S_2$) etc., or combinations thereof.

In embodiments, wherein the IN delivery gas-phase impermeable device is configured to deliver about 0.2 mL to about 1 mL medication intranasally.

In embodiments, the pliable rubber stopper forms a plurality of seals in circumferentially full contact between the inner surface of the vial and the rubber stopper, wherein each seal has a thickness of at least about 1 mm or more such that ingress of gaseous substance is effectively limited at a temperature between about 25° C. to about 40° C. and at a relative humidity between about 60% to about 75%.

In embodiments, the gas-phase impermeable seal is configured to prevent fluid exchange, microorganism, and/or particulate exchange between the medication solution contained within the vial and one or more other regions within the vial, such that undesirable contamination of the medication solution is prevented.

In embodiments, the gas-phase impermeable seal prevents contact between a gaseous substance contained within the vial and the medication solution. In embodiments, the gaseous substance is oxygen.

In embodiments, the base includes a top portion and a bottom portion positioned opposite to the top portion. The base further includes a plurality of hooks located at the top portion configured to initially engage with one or more of the plurality of slit openings of the injector barrel at a pre-delivery position and a plurality of latches extending from the base at the bottom portion configured to mechanically engage with the plurality of slit openings of the injector barrel at a post-delivery position. In embodiments, the plurality of hooks and the plurality of latches in the base are configured to produce tactile and/or audible feedback upon engagement with one or more of the plurality of slit openings in the pre-delivery position and/or at the post-delivery position.

In embodiments, the injector barrel is a first color, and the base is a second color, wherein the first color and the second color are different, such a dissimilarity in coloration between the injector barrel and the base facilitates convenient identification of a pre-delivery position and a post-delivery position.

In embodiments, actuation of the intranasal delivery gas-phase impermeable device involves compression of the base toward the injector barrel from a pre-delivery position to a post-delivery position thereby forcing the medication solution contained within the vial through the cannula and out of an intranasal tip of the injector barrel.

In embodiments, actuation of the intranasal delivery gas-phase impermeable device disperses the medication solution into a nasal cavity of a patient who is in one or more of an incapacitated position, an unconscious position, or lying in a supine position.

In other embodiments, provided is an intranasal delivery device for delivering a medication solution. The intranasal delivery device includes an injector barrel, a vial, and a base. The injector barrel includes an external tube with a plurality of transverse slit openings disposed circumferentially along the external tube; an inner tube that is homocentric with the external tube; a centering guide positioned lengthwise within the injector barrel; and a cannula in fluid communication with the medication solution secured in position by centrally bisecting the center guide. The vial is configured to couple with the injector barrel. The vial includes a base section. The vial is composed from a glass material or a plastic material. The vial further includes a pliable rubber stopper positioned above the base section of the vial, the pliable rubber stopper includes a plurality of seal rings, each seal ring having a geometry configured to form a gas-phase impermeable seal. A cannula is configured to centrally bisect the pliable rubber stopper. The vial includes a liquid medication disposed within the vial having volume of between about 0.2 mL and about 1.0 mL. The base has a top portion and a bottom portion positioned opposite to the top portion. The base is configured to engage with one or more of the plurality of transverse slit openings of the injector barrel during actuation of the intranasal delivery device. The base includes a plurality of hooks located at the top portion configured to engage with one or more of the plurality of transverse slit openings of the injector barrel at a pre-delivery position and a plurality of latches extending from the base at the bottom portion configured to engage with one or more of the transverse slit openings at a post-delivery position.

In other embodiments, provided is an IN delivery gas-phase impermeable device for delivery of between about 0.2 mL and about 1.0 mL of a medication solution. The IN delivery gas-phase impermeable device includes an injector barrel, a vial, and a base. The injector barrel includes a plurality of slit openings and a cannula in fluid communication with the medication solution. The vial is configured to couple with the injector barrel. The vial includes a pliable rubber stopper including a plurality of seal rings, each seal ring having a geometry configured to form a gas-phase impermeable seal with an internal circumferential surface of the vial. The cannula is configured to bisect the pliable rubber stopper. The base is configured to retain the vial in a fixed position suitable for insertion into the injector barrel by engagement of the base with one or more of the plurality of slit openings of the injector barrel.

Details of one or more implementations of the subject matter described in this disclosure are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE FIGURES

A full and enabling disclosure of the present invention, including the best mode thereof, directed to one of ordinary skill in the art, is set forth in the specification, which makes reference to the appended figures.

FIG. 17 shows a table comparing sample data measured for seal rings of the delivery device of FIG. 1 against dimensions of currently available devices.

Figure 1:
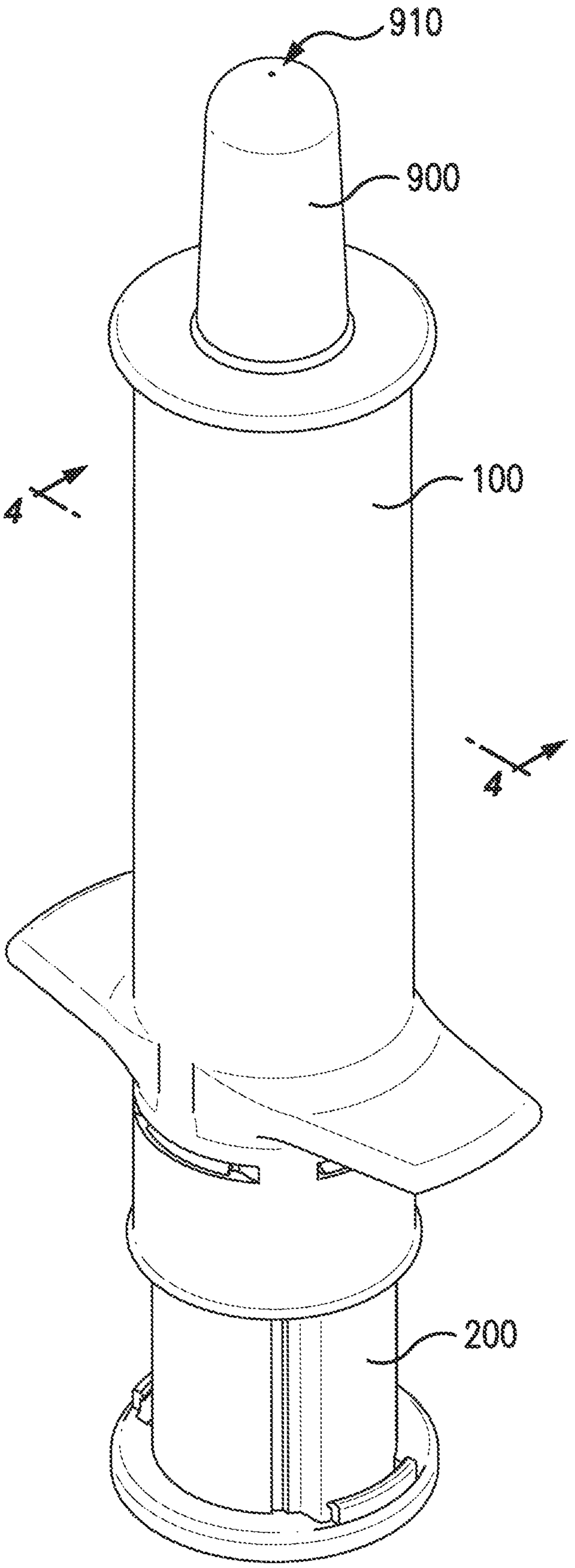
FIG. 1 shows a perspective view of delivery device for delivering a sterile medication in a pre-delivery position.

Repeat use of reference characters in the present specification and drawings is intended to represent the same or analogous features or elements of the present invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first," "second," and "third" may be used interchangeably to distinguish one component from another and are not necessarily intended to signify location or importance of the individual components, unless explicitly described as such. The terms "includes" and "including" are intended to be inclusive in a manner similar to the term "comprising." Similarly, the term "or" is generally intended to be inclusive (such as "A or B" is intended to mean "A or B or both").

Approximating language, as used herein throughout the specification and claims, is applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. For example, the approximating language may refer to being within a 10 percent margin.

Although conventional IN medication delivery devices are known, there still currently remains an unmet need for new IN delivery devices offering accessible ergonomics, increased stability, versatility, and ease of use, that are also able to deliver higher dosage quantities of medication. In addition, not all IN medication delivery devices can currently provide for sterile medication retention and delivery. This is largely due to the fact that the vial in which medication or medication solution is stored prior to delivery in such devices is typically not gas-phase impermeable against external elements. For example, there may be minute gaps between internal components permitting for certain gaseous substances, such as oxygen, to undesirably permeate into cavities within the vial containing the medication. Upon contact with oxygen, some medications may degrade, thereby limiting the useful lifespan of the IN delivery device and requiring medical personnel to constantly monitor the expiry dates of such devices.

Further, commercially available delivery devices may be constructed from relatively brittle components that are susceptible toward breakage during storage, transportation, or delivery of a medication. For instance, glass vials can be used to store medications within such devices. However, during administration, pressure must be exerted by the user on parts of the delivery device in order to successfully expel the medication from the device. Such pressure, when applied to moving parts of the device, can lead to breakage of materials used to construct the device or glass vials used to hold the medication. Such breakage can destroy the delivery device or otherwise render it inoperable, thereby preventing effective and timely administration of the medication, which can be especially undesirable and problematic in emergency situations. Further, having broken glass in the device can injure the patient using the device.

In addition, existing delivery devices may not be ergonomically designed to consider user preferences during self-administration or administration by other persons during, for example, emergency circumstances when the patient may be incapacitated. For example, some currently available nasal delivery devices may require the user to place their fingers on finger flanges located directly under the patient's nostril during administration of the medication from the device. In such instances, the user's fingers can interfere with the secure fit of the nasal delivery device within the patient's nostril, potentially leading to slippage of the device out from the patient's nostril, which may thereby lead to an inadequate or incorrect dose of medication being administered. Additionally, existing nasal delivery devices may also have a relatively short nasal tip that may also contribute to slippage of the tip out of the patient's nostril during medication administration. For example, placement of the user's fingers on the flanges extending from the nasal tip may cause this type of short nasal tip to slip out of a patient's nostril easily and undesirably during a dosage application. For example, force provided by the patient's fingers to hold the delivery device in a desired position within the patient's nostril may overcome force provided by the patient's thumb during medication administration. In this way, the relatively short nasal tip may slip or otherwise move out of the patient's nostril, thereby preventing a complete and accurate dosage delivery.

Further, existing IN delivery devices typically provide medication in 0.1 mL of solution, and thereby are unable to deliver relatively higher doses between 0.2 mL and 1 mL. Higher dosage volumes can facilitate the further dilution of medication formulation as needed. For certain medication formulations, lower medication concentration in a higher dosage volume can be desired. For example, increased dilution levels of the medication solution may permit for delivery of the medication solution to patients of different sizes including children weighing less than 40 kg. Current IN devices generally only provide medication in 0.1 mL dosage volumes, thereby preventing such dilution even in situations when a higher volume formulation is desired or medically appropriate. Also, existing IN devices may not effectively seal vials containing medication away from other portions of the IN device or the external atmosphere, thereby permitting contaminants to enter and contaminate the medication intended for usage.

Embodiments described herein overcome these and other challenges by providing—among other benefits—an IN delivery gas-phase impermeable device for delivery between 0.2 mL and 1.0 mL of a medication solution (such as either a sterile medication solution or a non-sterile medication solution). "Gas-phase impermeable" as used herein refers to storage of a medication solution in the IN delivery device such that substantially no ambient gaseous-phase components (e.g., gas) come into contact with the medication solution during storage. For example, the medication solution can be stored in the vial such that no ambient gases are capable of contacting the medication solution during storage. IN delivery devices as presently provided include a containment vessel, such as a vial, capable of containing a medication solution beneath a pliable rubber stopper. This stopper includes one or more seal rings (e.g., a plurality of seal rings) configured to reversibly expand and form one or more (e.g., a plurality of) interference-type fits against an internal circumferential surface of the vial thereby preventing undesirable fluid (e.g., gas) communication (e.g., contact) between the medication solution and other regions within the vial. Consequently, the pliable rubber stopper effectively seals the medication solution (such as medication solution in the liquid-phase) by preventing gaseous-phase substances, such as oxygen gas, from contacting and undesirably contaminating the medication solution. Alternatively put, the vial further comprises a bottom section and the vial is configured to store the medication solution between the pliable rubber stopper and the bottom section of the vial such that the gas-phase impermeable seal prevents communication of a gaseous substance contained within the vial and the medication solution.

The IN delivery gas-phase impermeable device can be composed of multiple interlocking components. For instance, the gas-phase impermeable IN device may be assembled from such interlocking components by hand by a prospective user, emergency medical technician or other professional, into a complete device capable of injecting the medication solution into a nasal cavity of a patient. The interlocking components include, at a minimum, an injector barrel, a vial, and a base. Generally, the base may retain the vial and be inserted, with the vial, lengthwise into the injector barrel during assembly and/or actuation of the IN delivery gas-phase impermeable device. More particularly, the injector barrel includes multiple slit openings disposed circumferentially along the injector barrel and may also include a tip capable of insertion into a nostril of a patient that forms an interference-type fit within a circumference of the nostril of the patient.

In embodiments, the injector barrel includes a center guide, optionally made from a rigid material, that is positioned lengthwise within the injector barrel and a cannula in fluid communication with the medication solution that is secured in a fixed position by the center guide. The vial is configured to couple with the injector barrel. The vial contains a pliable rubber stopper including multiple seal rings, each seal ring has a geometry configured to form a gas-phase impermeable seal with an internal surface of the vial. The gas-phase impermeable seal is configured to prevent fluid, microorganism, and particulate exchange between the medication solution contained within the vial and other regions within the vial and thereby is capable of preventing undesirable contamination of the medication solution. The cannula can be configured to bisect the pliable rubber stopper. Further, the base is configured to reversibly engage with one or more of the slit openings of the injector barrel during actuation of the IN delivery gas-phase impermeable device.

In some embodiments, the base has a top portion and a bottom portion positioned opposite to the top portion. The base may include multiple hooks (e.g., claw-shaped hooks) located at the top portion that are configured to initially engage with one or more of the slit openings of the injector barrel at a pre-delivery position. In addition, the base may include multiple latches extending from the base at the bottom portion that are configured to engage or mate (e.g., irreversibly mate) with one or more of the slit openings at a post-delivery position. The multiple hooks and the multiple latches are configured to produce a tactile and/or audible feedback upon engagement with one or more of the slit openings at separation from pre-delivery position and at the post-delivery position.

In addition, actuation of the IN delivery gas-phase impermeable device involves compression of the base toward the injector barrel from the pre-delivery position to the post-delivery position thereby forcing the medication solution contained within the vial through the cannula and out of the injector barrel. In this way, actuation of the IN delivery gas-phase impermeable device disperses the medication solution into a nasal cavity of a patient who may be in, for example, one or more of incapacitated, unconscious, or lying in a supine position.

In some embodiments, the injector barrel has a first color (such as white) and the base has a second color (such as green) dissimilar to the first color. This dissimilarity in coloration between the injector barrel and the base facilitates convenient identification of the initial pre-delivery position and the post-delivery position. In addition, the base can be wider than the injector barrel and thereby facilitate convenient finger-pressing actuation of the IN delivery gas-phase impermeable device. More specifically, a pair of finger flanges may extend laterally away from the injector barrel, each finger flange positioned diametrically opposite to each other and configured to support a user's finger. For example, a user's thumb may be placed on the base and two of the user's fingers, such as his or her index finger and middle finger, may be placed on finger flanges extending laterally outwardly from the injector barrel, thereby permitting the user to push the base upward with his or her thumb towards the finger flanges effectively compressing the base toward and into the injector barrel.

The injector barrel may also include multiple ribs, each rib disposed lengthwise on an inner surface of the injector barrel. The multiple ribs are collectively configured to hold the vial in a fixed clockwise and counterclockwise position within the injector barrel. More specifically, the multiple ribs compress against an external circumferential surface of the vial to form an interference-type fit that prevents rotational motion of the vial in either a clockwise or counterclockwise direction relative to an original insertion position of the base into the vial. As shown throughout the figures, embodiments are directed to a delivery device for delivering a medication. The delivery device may be used to inject a sterile medication. In addition, embodiments disclosed herein facilitate the routine and accurate delivery of greater quantities (such as a larger volume) of sterile medication (such as 0.2 mL to 1 mL) than otherwise are typically provided by current commercially available IN delivery devices, which may be restricted to deliver 0.1 mL medication.

Notably, delivery of between about 0.2 mL and about 1.0 mL of the medication solution permits for increased dilution levels of the medication solution relative to conventional 0.1 mL dosage quantities. Such increased dilution levels of the medication solution permit for delivery of the medication solution to patients of different sizes including children weighing less than 40 kg. In some examples, the medication solution includes at least one active pharmaceutical ingredient (APIs) including epinephrine ($C_9H_{13}NO_3$), ketorolac ($C_{15}H_{13}NO_3$), naloxone ($C_{19}H_{21}NO_4$), sildenafil ($C_{22}H_{30}NO_4S$), tadalafil ($C_{22}H_{19}N_3O_4$), phytonadione ($C_{31}H_{46}O_2$), insulin aspart ($C_{256}H_{381}N_{65}O_{79}S_6$), nitroglycerin ($C_3H_5N_3O_9$), teriparatide ($C_{181}H_{291}N_{55}O_{51}S_2$), or combinations thereof.

Another embodiment provided includes an IN delivery device for delivering a medication solution. The IN delivery device includes an injector barrel, a vial, and a base. More particularly, the injector barrel includes multiple transverse slit openings disposed circumferentially along the injector barrel, a center guide that is positioned lengthwise within the injector barrel, and a cannula in fluid communication with the medication solution that is secured in a fixed position by centrally bisecting the center guide. The vial can be configured to couple with the injector barrel.

In such embodiments, the vial includes a base section and a pliable rubber stopper. The pliable rubber stopper is positioned above the base section and includes multiple seal rings. Each seal ring has a geometry configured to form a gas-phase impermeable seal with an internal circumferential surface of the vial. The vial also includes between 0.2 mL and 1.0 mL of a medication solution positioned between the base section and the pliable rubber stopper. The cannula centrally bisects the pliable rubber stopper.

The IN delivery device also includes a base having a top portion and a bottom portion positioned opposite to the top portion. The base configured to engage with one or more of the multiple transverse slit openings of the injector barrel during actuation of the IN delivery device. More particularly, the base can include multiple hooks (e.g., claw-type hooks) located at the top portion that are configured to engage with the one or more of the multiple of transverse slit openings of the injector barrel at an initial pre-delivery position. In addition, the base includes multiple latches extending from the base at the bottom portion that are configured to irreversible lock with one or more of the multiple transverse slit openings at the post-delivery.

Yet another embodiment of the present disclosure includes an IN delivery gas-phase impermeable device for delivery of between about 0.2 mL and about 1.0 mL of a medication solution. The IN delivery gas-phase impermeable device includes an injector barrel including multiple slit openings, a cannula in fluid communication with the medication solution, and a vial configured to mechanically couple with the injector barrel. The vial includes a pliable rubber stopper including multiple seal rings. Each seal ring has a geometry configured to form a gas-phase impermeable seal with an internal circumferential surface of the vial. The cannula bisects the pliable rubber stopper. In addition, the IN delivery gas-phase impermeable device includes base configured to retain the vial in a fixed position suitable for insertion into the injector barrel by engagement of the base with one or more of the slit openings of the injector barrel.

Figure 2:
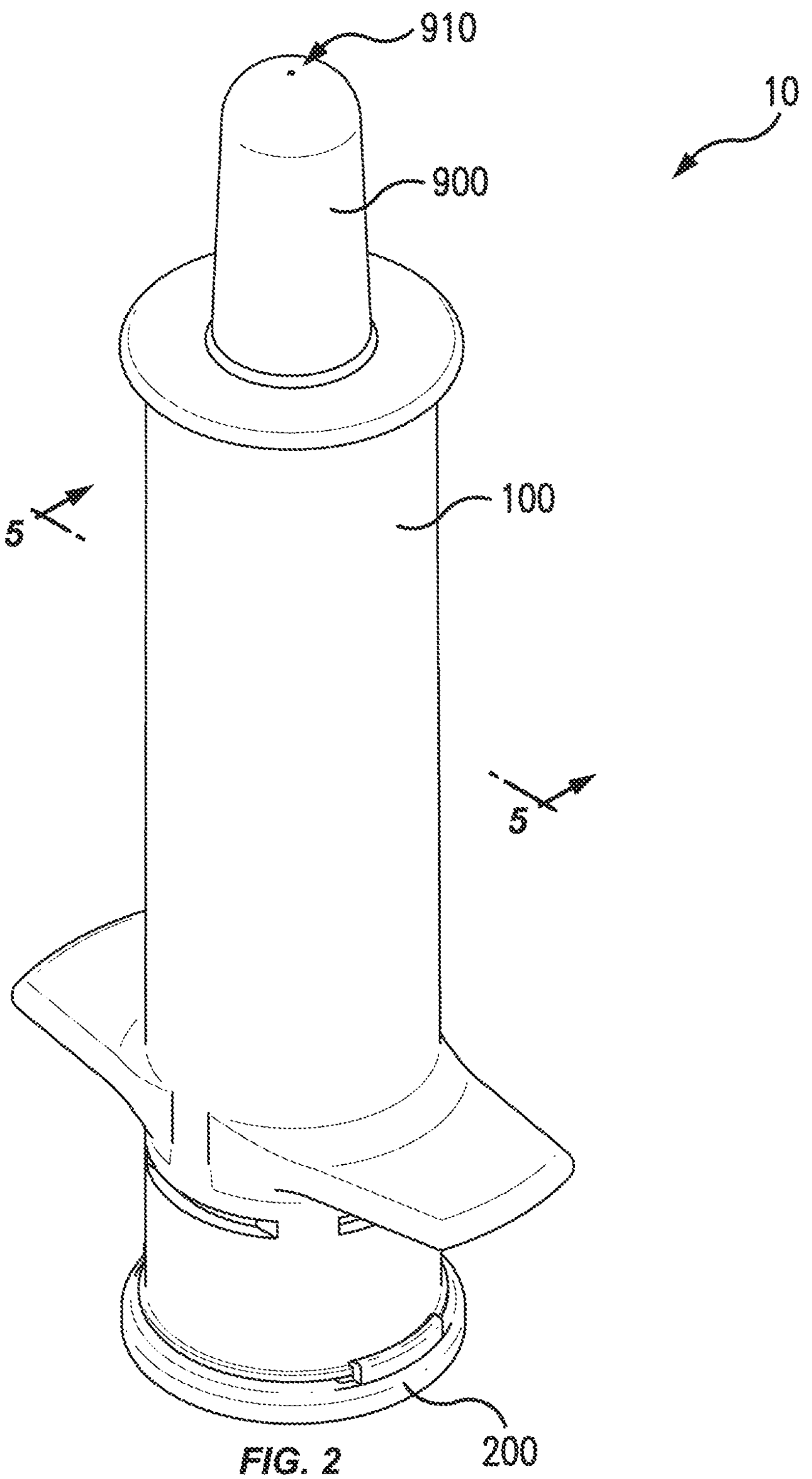
FIG. 2 shows a perspective view of the delivery device of FIG. 1 in a post-delivery position.

FIG. 1 illustrates delivery device 10 (also referred to herein as an "IN delivery gas-impermeable device") in a pre-delivery state (such as before any medication has been dispensed also referred to herein as an "initial pre-dispersement position"). In some instances, medication delivered by delivery device 10 may be sterile medication. Alternatively, in some other instances, the medication is non-sterile medication. Example medication that may be delivered by delivery device 10 includes an active pharmaceutical ingredient (API) selected from epinephrine ($C_9H_{13}NO_3$), ketorolac ($C_{15}H_{13}NO_3$), Naloxone ($C_{19}H_{21}NO_4$), sildenafil ($C_{22}H_{30}N_6O_4S$), tadalafil ($C_{22}H_{19}N_3O_4$), phytonadione ($C_{31}H_{46}O_2$), insulin aspart ($C_{256}H_{381}N_{65}O_{79}S_6$), nitroglycerin ($C_3H_5N_3O_9$), teriparatide ($C_{181}H_{291}N_{55}O_{51}S_2$), or combinations thereof. FIG. 2 illustrates delivery device 10 in a post-delivery state (such as after all medication has been dispensed also referred to herein as a "final post-dispersement position"). Delivery device 10 may include injector barrel 100, base 200, and cap 900. An outlet 910 is disposed at the tip of the cap 900 through which the medication is dispensed from delivery device 10. Base 200 may be slidably coupled to injector barrel 100. In some embodiments, base 200 may slide relative to injector barrel 100 from a pre-delivery position, shown in FIG. 1, to a post-delivery position, shown in FIG. 2. Delivery device 10 may be a device for delivering a medication to a patient (such as a syringe or an IN injector). In some embodiments, delivery device 10 may be a device for delivering a medication by IN administration. In some embodiments, delivery device 10 is a nasal injector capable of delivering medication to a nasal passage of a patient.

Figure 3:
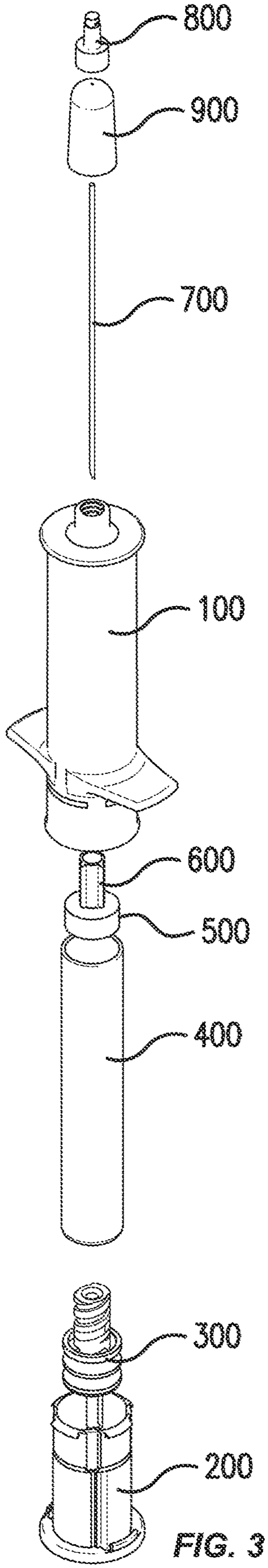
FIG. 3 shows an exploded view of the delivery device of FIG. 1.
Figure 4A:
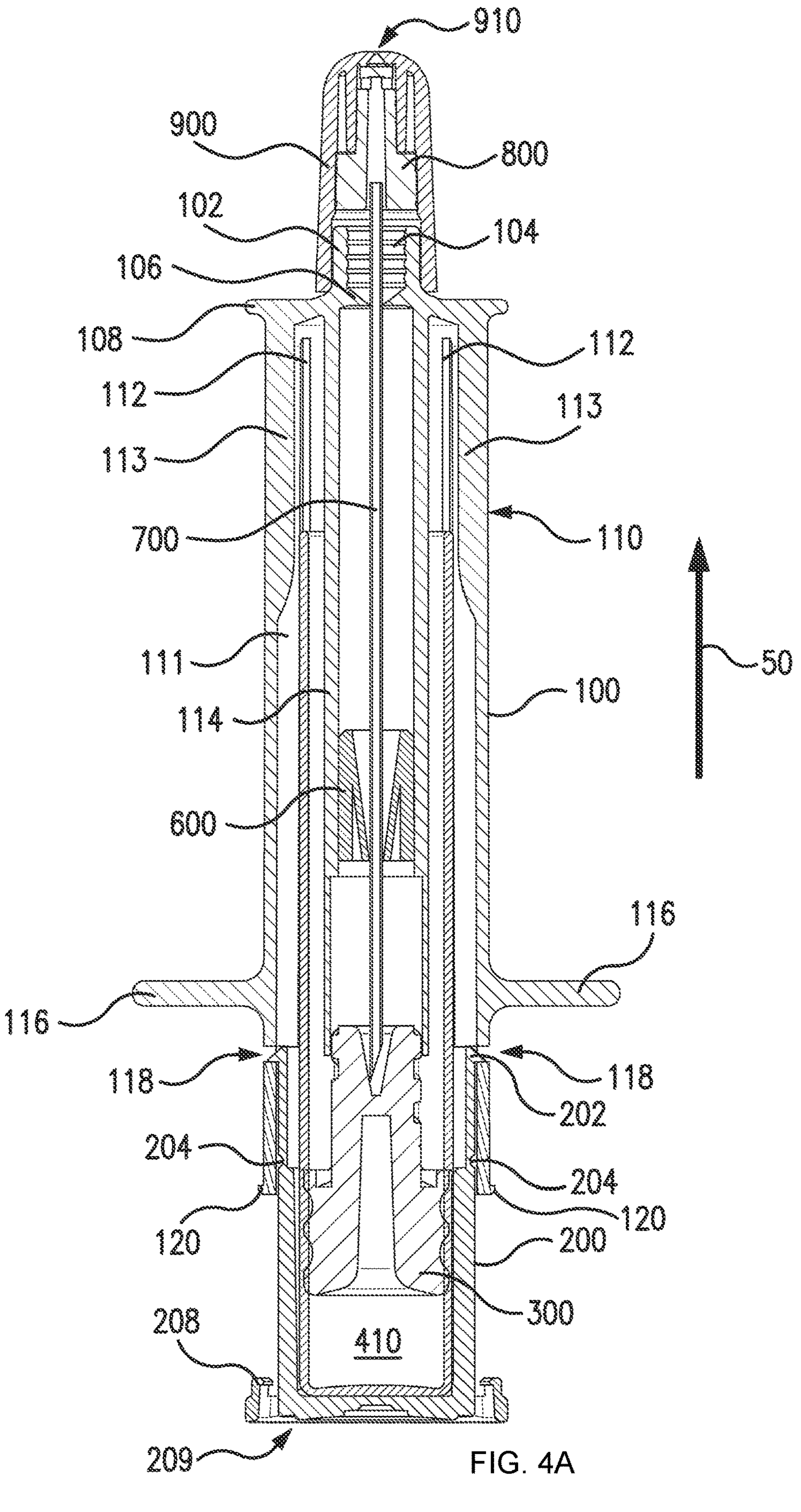
FIG. 4A shows a cross-section of the delivery device of FIG. 1 taken along an X-Y plane at line 4-4.
Figure 4B:
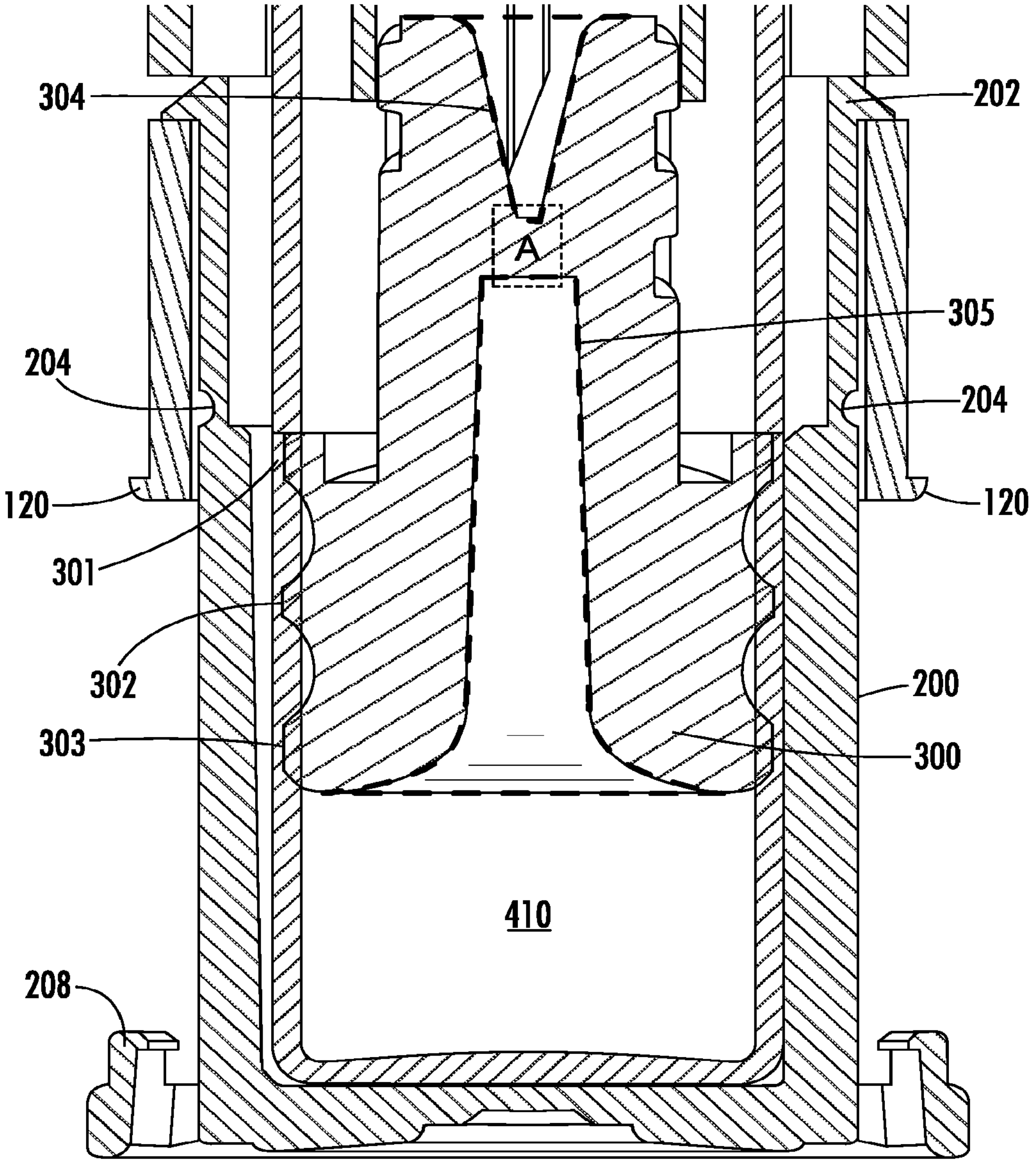
FIG. 4B shows a detailed view of a portion of the delivery device of FIG. 4A.
Figure 4C:
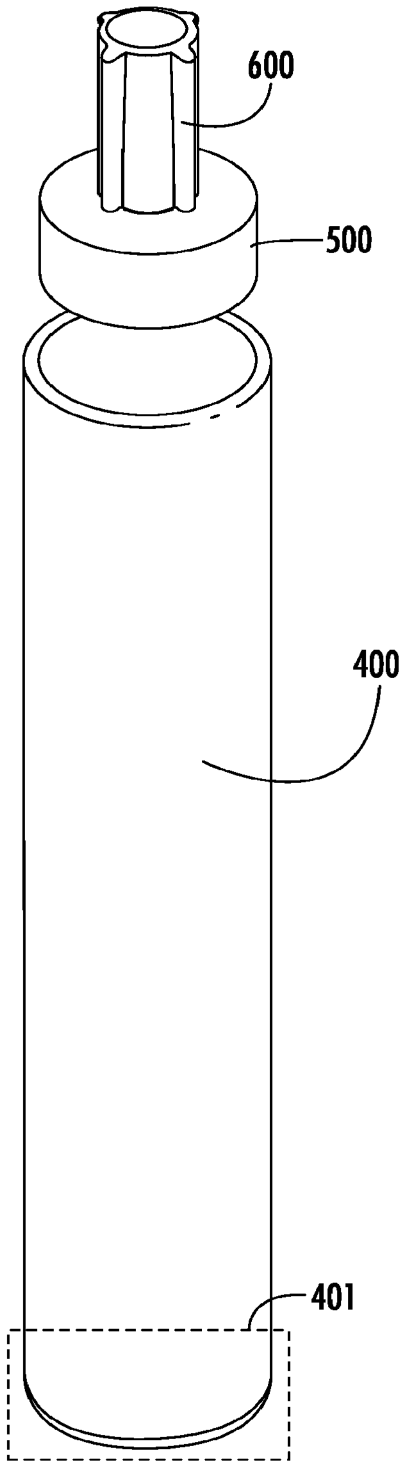
FIG. 4C shows a detailed view of a portion of the delivery device of FIG. 3.
Figure 5:
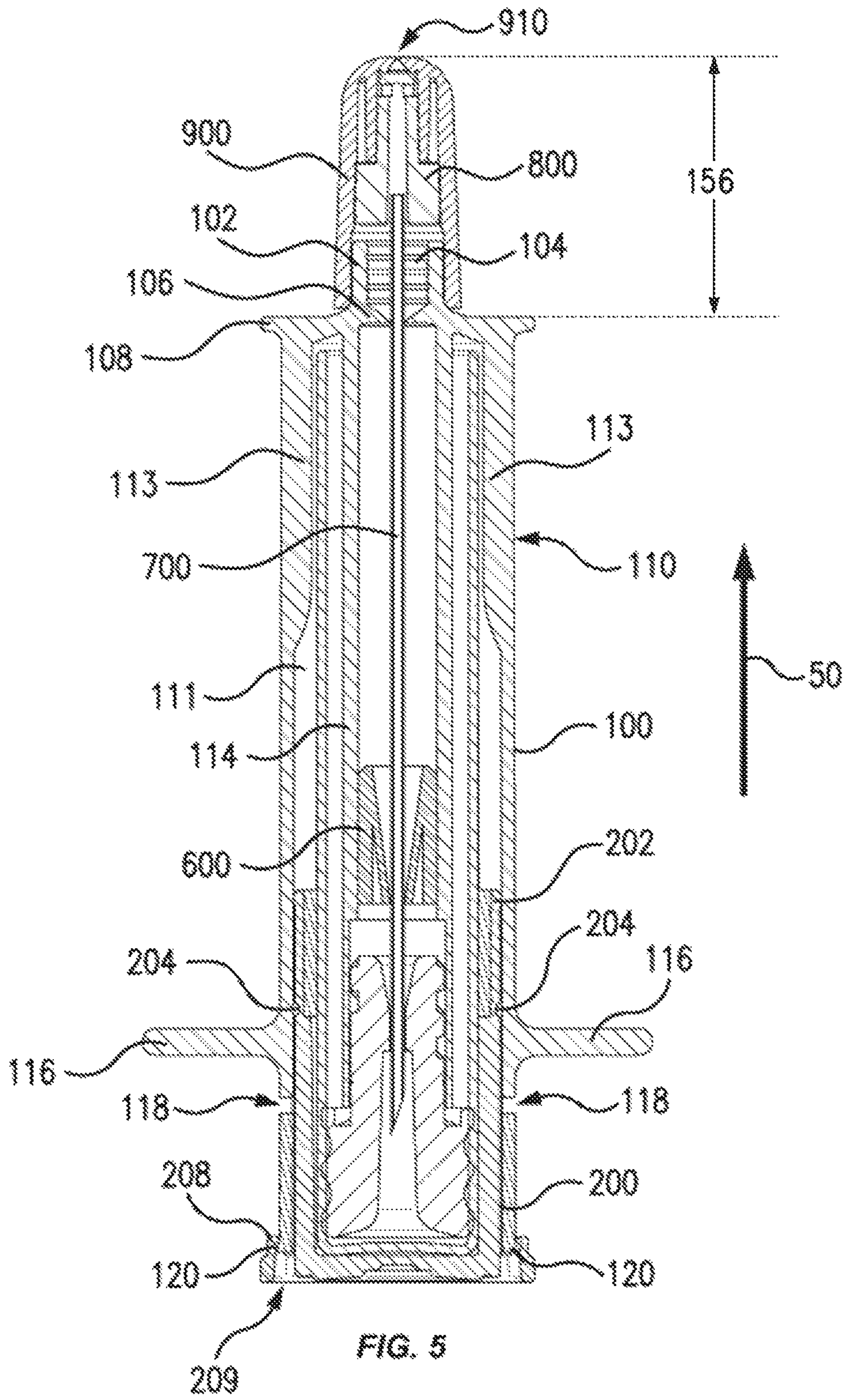
FIG. 5 shows a cross-section of the delivery device of FIG. 2 taken along an X-Y plane at line 5-5.

FIG. 3 illustrates an exploded view of delivery device 10 shown in, for example, FIGS. 1 and 2. FIG. 4A shows a cross-section of delivery device 10 taken along line 4-4. FIG. 4B shows a detailed view of the cross section of delivery device 10 shown in FIG. 4. FIG. 4C shows a detailed view of vial 400 shown in FIG. 3. FIG. 5 shows a cross-section of delivery device 10 taken along line 5-5. Delivery device 10 may include injector barrel 100, base 200, stopper 300, which may be a pliable rubber stopper, vial 400, guide 600, nozzle 800, and cap 900. In some embodiments, when delivery device 10 is in the pre-delivery state, as shown in FIG. 1, delivery device 10 includes liquid 500, which may be contained within vial 400 beneath stopper 300. In some embodiments, delivery device 10 is fitted with cannula 700 shown in, for example, FIG. 3. The liquid 500 can include a medication solution.

Referring now to FIG. 3, stopper 300 is produced from a pliable material, such as rubber, which may reversibly deform upon compression. For example, stopper 300 may be compressed and thereby squeezed into vial 400 to later expand diametrically outwards to compress against an internal surface (not shown in FIG. 3) of vial 400. In this manner, the geometry (such as the diameter) of stopper forms an interference, friction, or pressed fit with the internal surface of vial 400. More specifically, stopper 300 is held in position within the vial 400 above a bottom of vial 400 by this type of pressed fit. Alternatively, stopper 300 may be described as being "well-fit" the inner diameter of the glass vial. When delivery device 10 is in the pre-delivery state, as shown in FIG. 4A-C, vial 400 may include interior volume 410 defined in part by vial 400 and in part by stopper 300. Consequently, vial 400 may hold a liquid 500 within interior volume 410 of vial 400, where liquid 500 may be a sterile medication for delivery to a patient using delivery device 10.

In some embodiments, stopper 300 may have multiple vertically oriented ring seals. For example, FIG. 4B depicts a circumference of a rubber stopper 300 having at least three (3) seal rings 301, 302 and 303 configured to form a pressed fit within vial 400, thereby retaining stopper 300 in a fixed initial position above interior volume 410. The width of the seal rings 301, 302 and 303 should be sufficiently large to warrant the seal of both liquid and gas phase components inside vial 400 such that the contents inside the vial (such as in solution and the headspace) cannot exchange with substances (such as oxygen) prevalent in the environment (such as outside the vial). Alternatively put, stopper 300 may include one or more, such as a plurality of seal rings 301, 302, and 303, each seal ring having a geometry configured to form a gas-phase impermeable seal with an internal surface of the vial. In addition, stopper 300 may include upper region 304 and lower region 305. In embodiments, each region can represent a cut out from the stopper 300. That is, upper region 304 and lower region 305 can define void spaces within stopper 300. More specifically, upper region 304 can be substantially shaped as an inverted triangle or trapezoid and lower region 305 can be substantially shaped as an upright triangle or trapezoid. Further, upper region 304 can be sized to receive cannula 700 (shown in FIG. 4A-C), which may penetrate through region A positioned between upper region 304 and lower region 305. In embodiments, region A is relatively thin to facilitate convenient penetration of stopper 300 into interior volume 410 during, for example, actuation of delivery device 10. In embodiments, the total volume of material through which cannula 700 must penetrate through stopper 300 may be calculated as shown below in Equation 1:

$$\Delta V = \Delta h \times A \quad \text{(Eq. 1)}$$

Where "ΔV" denotes change in volume, "Δh" denotes change in height, and "A" denotes cross-sectional area. The shorter height h and smaller cross-sectional area "A" of region A result in a smaller change in volume ΔV, resulting in: (i) a reduction in necessary break force at use (such as during penetration of region A of stopper 300 by cannula 700); and (ii) a reduction of fluctuation of dead volume within vial 400 of delivery device 10 at delivery.

FIG. 4C illustrates an expanded view of vial 400 shown in FIG. 3. In some embodiments, vial 400 has a uniform cylindrical shape having a cross-sectional area of a circle or disc and can be made from glass materials and/or plastic materials. More specifically, in some embodiments, vial 400 is produced such that there are no glass components on inner surfaces of vial 400 having relatively low boiling points. In addition, vial 400 defines a bottom portion 401, which is flat and capable of temporarily retaining liquid 500. During actuation of delivery device 10, stopper 300 may be penetrated by cannula 700 at region A and thereby also be pushed downward within vial 400 toward bottom portion 401. Consequently, liquid 500 is squeezed by stopper 300 into cannula 700 and pushed up through cannula 700 to disperse out of outlet 910 into a patient's nostril. The shape of stopper 300, including upper region 304 and lower region 305 and the shape of vial 400 result in minimization of dead volume within vial 400. Consequently, the dead volume within vial 400 when stopper 300 is compressed against bottom portion 401 is fixed and minimal when compared to conventional syringes.

Figure 6:
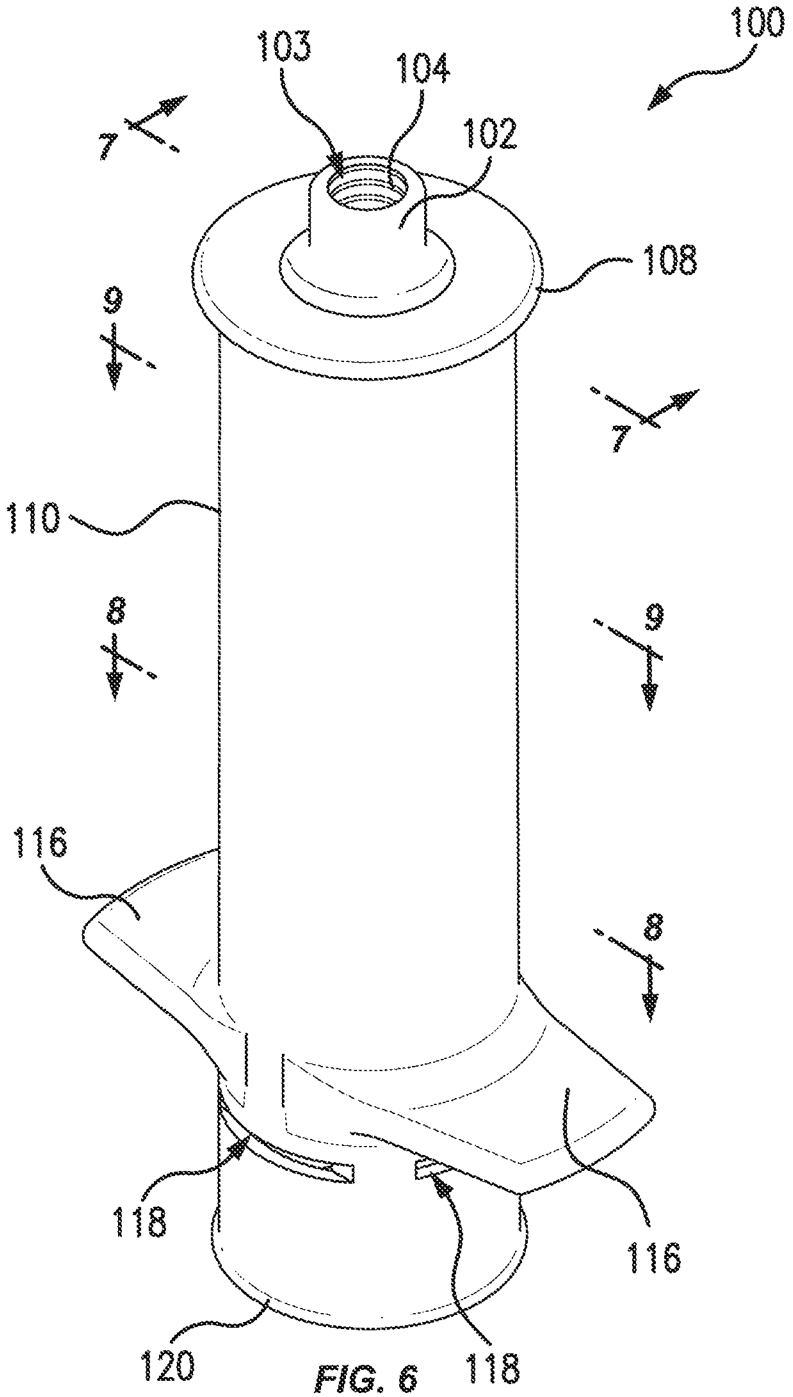
FIG. 6 shows a perspective view of a barrel of the delivery device of FIG. 1.
Figure 7:
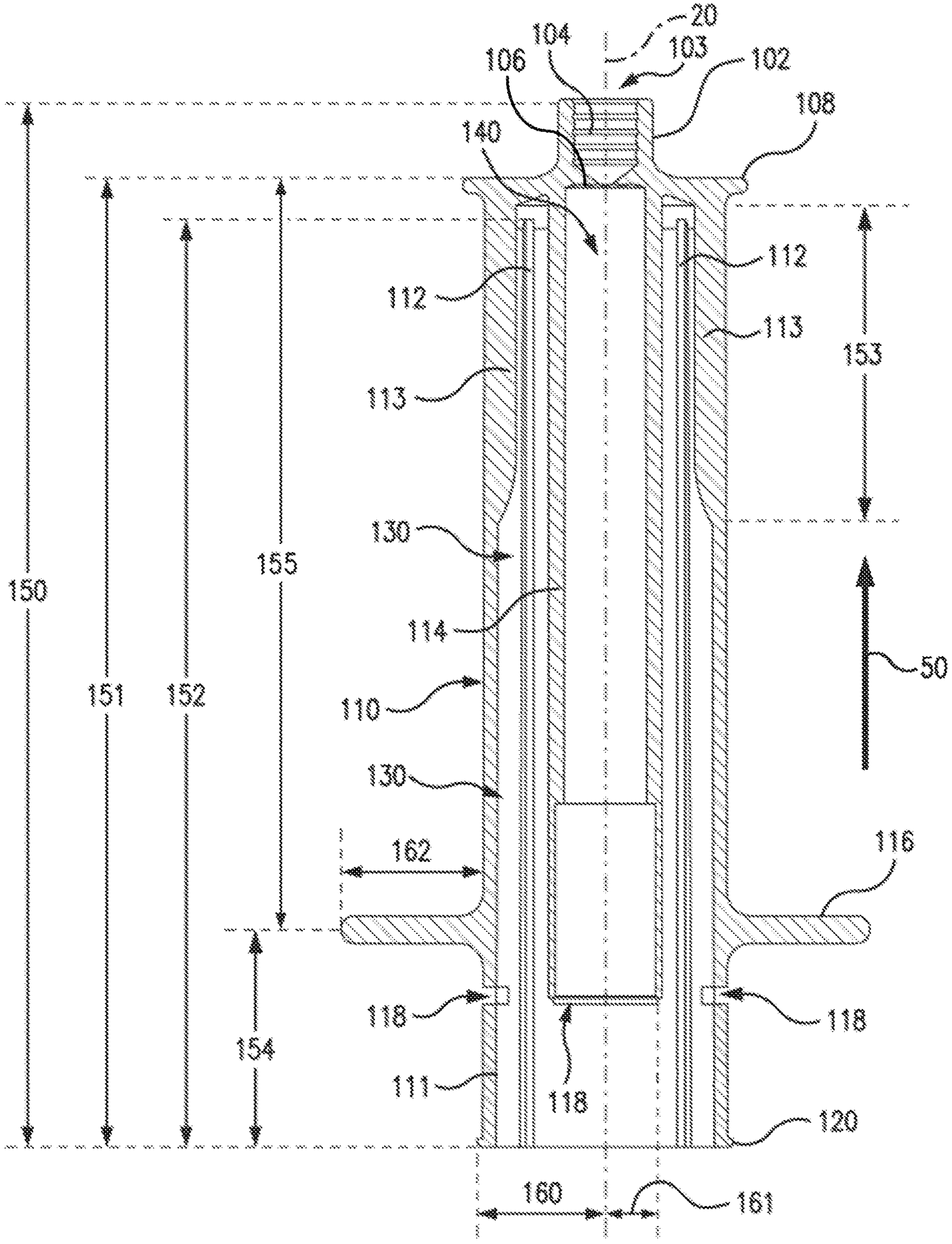
FIG. 7 shows a cross-section of the barrel of FIG. 6 taken along an X-Y plane at line 7-7.

FIGS. 6-9 illustrate various views of injector barrel 100, which has a longitudinal dimension extending in the direction of arrow 50 along axis 20. In some embodiments, injector barrel 100 may include an upward projection 102 extending vertically outward along the direction of arrow 50 along axis 20 as shown in FIG. 5. Upward projection 102 may include an opening 103 and ribs 104 that project inward from an inner surface of upward projection 102 as shown in FIG. 6. In some embodiments, ribs 104 are oriented perpendicular to axis 20. As shown in FIG. 5, injector barrel 100 may include inward flange 106 that defines an opening through which cannula 700 may extend. In addition, injector barrel 100 may include flange 108, which may be positioned adjacent to and/or against the external circumference of a patient's nostril to, for example, prevent the cap 900 from being inserted too far into the patient's nostril, or from otherwise undesirably slipping out. That is, during dispensation of sterile medication from the delivery device 10, flange 108 may abut against external surfaces of the nose and/or of the nostril and thereby compress against the nose of a patient. More particularly, cap 900 may be inserted within the patient's nostril and be substantially held in a desired position by flange 108. Injector barrel 100 may have an outer surface 110 and inner surface 111, which may be positioned opposite to the outer surface 110 along axis 20 as shown in FIG. 7. Inner surface 111 at least partially defines an inner volume of injector barrel 100. Inner surface 111 of injector barrel 100 may include a first plurality of ribs (such as long ribs 112) projecting radially inward from inner surface 111 toward axis 20; and, in addition, inner surface 111 of injector barrel 100 may include a second plurality of ribs (such as short ribs 113) projecting radially inward from inner surface 111 toward axis 20. In some embodiments, long ribs 112 and short ribs 113 are integral with injector barrel 100 such that injector barrel 100, long ribs 112, and short ribs 113 form a unitary structure. Injector barrel 100 may include inner tube 114 that extends from an upper portion of injector barrel 100 into an interior volume of injector barrel 100. In some embodiments, inner tube 114 is coaxial with outer walls of injector barrel 100. In some embodiments, inner tube 114 is integral with injector barrel 100 such that injector barrel 100 and inner tube 114 form a unitary structure. In addition, in some embodiments, inner tube 114 has radius 161, which is smaller than radius 160 of the injector barrel 100.

Injector barrel 100 may have one or more (such as a pair) finger flanges 116 extending outwardly from the injector barrel 100 and positioned perpendicular relative to axis 20. In some embodiments, finger flanges 116 include a first finger flange extending in a first direction perpendicular to axis 20 and a second finger flange extending in a second direction opposite the first direction. Alternatively put, finger flanges 116 extend laterally away from the injector barrel. Each finger flange 116 may be positioned diametrically opposite to each other and be capable of supporting a finger, such as of a patient for self-administration or of another person. Injector barrel 100 may have one or more slit openings 118, at least some of which extend inwardly toward axis 20 (such as shown in FIG. 7). In some embodiments injector barrel 100 includes at least two slit openings 118 (such as at least four slit openings 118). Slit openings 118 may have a long axis oriented in a direction perpendicular to axis 20. For instance, slit openings 118 can have a long axis oriented in a direction extending at least partially radially around the circumference of the injector barrel 100. Injector barrel 100 may include a bottom flange 120 that extends out from outer surface 110.

As shown in FIG. 7, injector barrel 100 may have an overall height 150 measured along a central Y-axis (such as axis 20); a height 151 from flange 108 to bottom flange 120; a height 152 from the top of long ribs 112 to the bottom of long ribs 112; a height 153 from the top of short ribs 113 to the bottom short ribs 113; a height 155 from flange 108 to finger flanges 116; and a height 154 from finger flanges 116 to bottom flange 120. Notably, in certain embodiments, height 155 (such as shown in FIG. 7) is greater than height 156 (such as shown in FIG. 5). For example, the ratio of height 155 to height 156 is from about 5:1 to about 1.5:1, such as from about 4:1 to about 2:1, such as about 3:1. Having the specific ratio of height 155 (such as the height of the injector barrel 100) to height 156 (such as the height of the cap 900) provides a more ergonomic configuration for the user. Indeed, injector barrel 100 with height 155 provides more barrel length for the user to hold while dispensing medication from the delivery device 10. Such a feature also enables the user to more securely hold the device while dispensing medication, such that accurate dispensing is achieved.

For example, finger flanges 116 may be sized and positioned to allow a user to grip delivery device 10 using finger flanges 116, such as by placing the index finger on one flange and the middle finger on the other flange. As shown in FIG. 7, finger flanges 116 may be positioned at a height 154 above bottom flange 120. In some embodiments, height 154 is about 10 mm to about 20 mm (such as about 12 mm to about 16 mm). In some embodiments, height 154 is about 14 mm. Finger flanges 116 may extend laterally out from outer surface 110 of injector barrel 100 by a distance 162. In some embodiments, distance 162 is about 5 mm to about 15 mm (such as about 8 mm to about 12 mm). In some embodiments, distance 162 is about 9 mm. Notably, height 155 separates flange 108 from finger flanges 116. Aspects of the present disclosure recognize that having finger flanges 116 spaced away from flange 108 allows the user to dispense sterile medication from the delivery device 10 without having his or her fingers located at or near the nostril, which thereby provides stabilization of the delivery device 10 during sterile medication administration. This configuration may present a departure from conventional IN sterile medication delivery devices, which may have only a single contact surface intended for both placement (such as juxtaposition) next to the nostril and for grasping by the patient's fingers. This single contact surface may become unstable when, for example, the user provides more downward force by his or her fingers on the single contact surface relative to upward force provided by his or her thumb, as necessary to inject sterile medication into the nostril and nasal cavity. This force imbalance may result in undesirable movement of the IN delivery device, such as slipping out of the patient's nostril.

For instance, referring to FIG. 5, cap 900 may have a height 156 extending from flange 108 to the top of cap 900. In some embodiments, height 156, may be sized to fit (such as by a pressed-fit) into the nostril of a patient, extend into the patient's nasal cavity, and/or have at least some of the physical dimensions described below. Consequently, cap 900 of the delivery device 10 may remain in a desired medication delivery position within a patient's nostril during medication delivery processes without inadvertently and undesirably slipping out of the patient's nostril. That is, height 156 of cap 900 may be sized to uniquely (such as compressively) fit in and remain within the patient's nostril, thereby, for example, at least partially overcoming force applied by the patient's fingers on finger flanges 116 away from the patient's nostril, to thereby avoid slipping out of the patient's nostril.

Referring to at least FIGS. 4A-C and 7, in some embodiments, delivery device 10 includes at least two long ribs 112 (such as at least three long ribs 112 or at least four long ribs 112). In some embodiments, delivery device 10 includes at least two short ribs 113 (such as at least three short ribs 113 or at least four short ribs 113). In some embodiments, delivery device 10 includes four long ribs 112 and four short ribs 113. Long ribs 112 and short ribs 113 may have longitudinal dimensions extending in the direction of axis 20. The longitudinal dimension of long ribs 112 may be equal to height 152, and the longitudinal dimension of short ribs 113 may be equal to height 153. In some embodiments, as shown in FIG. 7, height 152 is greater than height 153. In some embodiments, height 152 is about 55 mm to about 70 mm (such as about 60 mm to about 65 mm). In some embodiments, height 152 is about 62 mm. In some embodiments, height 153 is about 15 mm to about 30 mm (such as about 20 mm to about 25 mm). In some embodiments, height 153 is about 21 mm.

Figure 8:
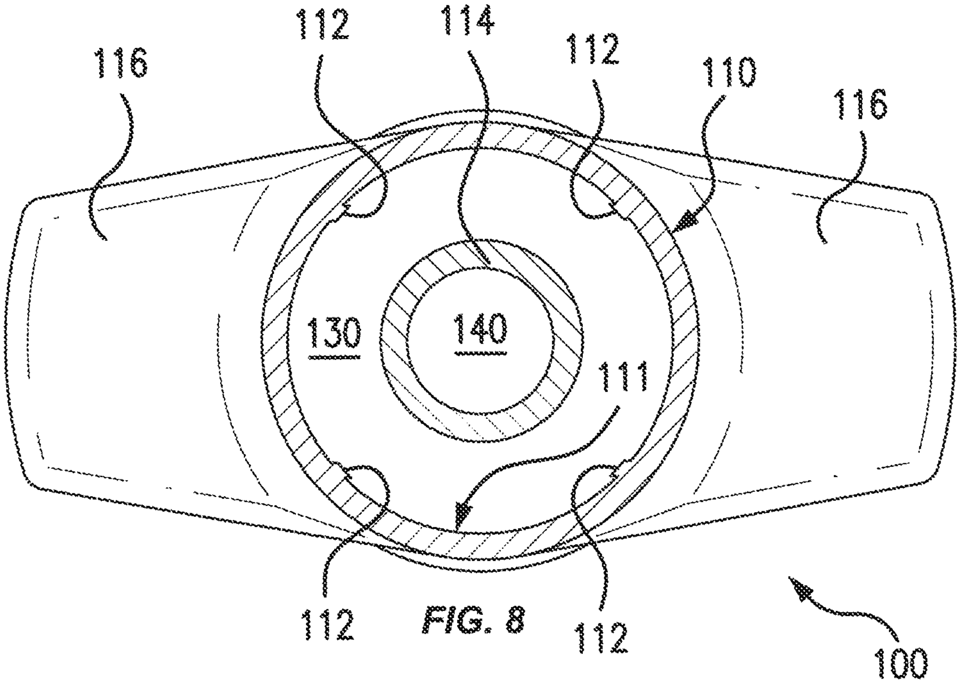
FIG. 8 shows a cross-section of the barrel of FIG. 6 taken along an X-Z plane at line 8-8.
Figure 9:
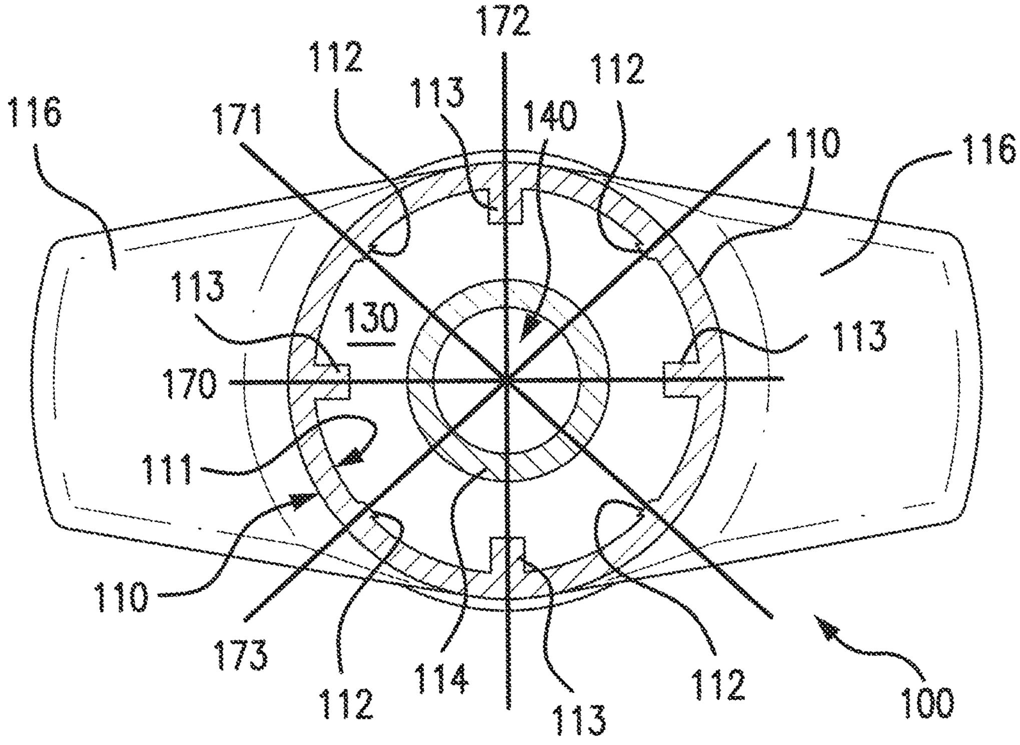
FIG. 9 shows a cross-section of the barrel of FIG. 6 taken along an X-Z plane at line 9-9.
Figure 10:
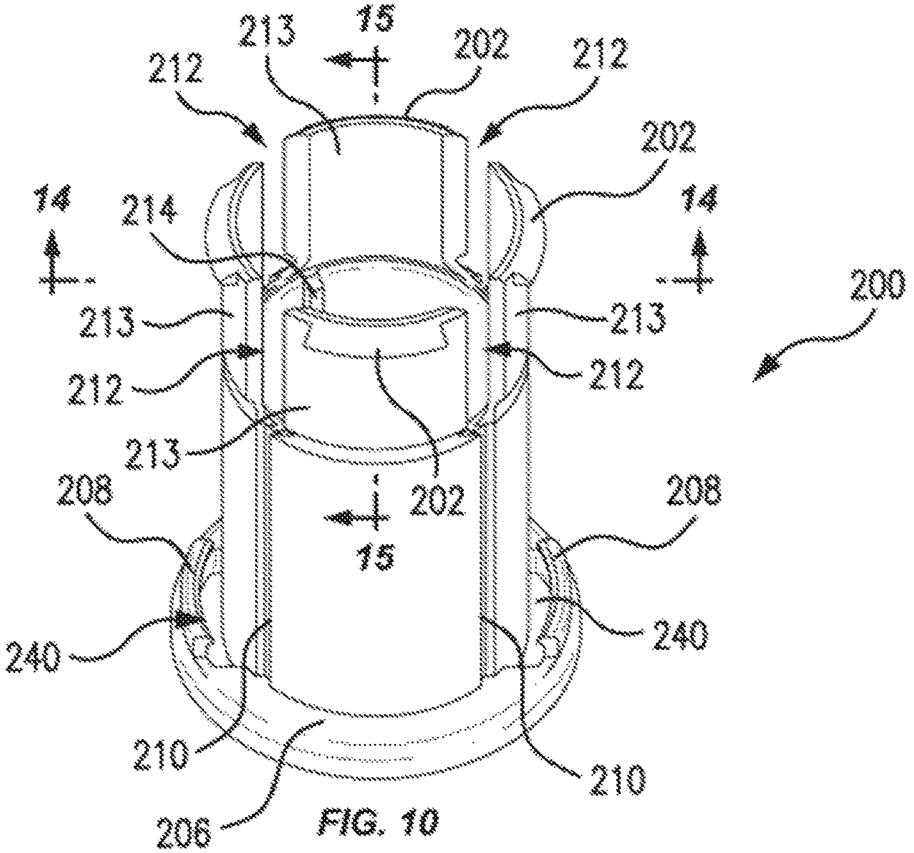
FIG. 10 shows a perspective view of a base of the delivery device of FIG. 1.

FIG. 8 illustrates a cross-section view of injector barrel 100 taken along line 8-8 (as shown in FIG. 6). As shown in FIG. 8, injector barrel 100 may include an interior volume 130 defined at least in part by the inner surface 111 of the outer walls of injector barrel 100 and inner tube 114 and an interior volume 140 defined at least in part by inner tube 114, which may be coaxial with injector barrel 100. One or more long ribs 112 are disposed on the inner surface 111 and extend radially inward. Notably, at a location of the injector barrel 100 taken along line 8-8, there are no short ribs 113 disposed on the inner surface 111 of the injector barrel 100. A coordinate axis system is overlaid on the cross-section shown in FIG. 9. In addition, FIG. 9 illustrates a cross-section view of injector barrel 100 taken along line 9-9 (as shown in FIG. 6) on a horizontal X-Z plane defined by X-axis 170 and a Z-axis 172, with the origin defined by the intersection of central Y-axis (such as axis 20), X-axis 170, and Z-axis 172. As shown in FIG. 9, long ribs 112 and short ribs 113 may be spaced evenly around inner surface 111 of injector barrel 100. In some embodiments, long ribs 112 and short ribs 113 are arranged in an alternating pattern around inner surface 111 of injector barrel 100. In some embodiments, each of long ribs 112 is positioned at an angle 45 degrees relative to the X- and Z-axes (such as along lines 171 and 173). In some embodiments, each of short ribs 113 is positioned at an angle 0 degrees relative to X-axis 170 and Z-axis 172.

As shown in FIG. 9, short ribs 113 may project radially inward by a greater distance than long ribs 112. In some embodiments, long ribs 112 project radially inward about 0.1 mm to about 0.6 mm (such as about 0.2 mm to about 0.4 mm). In some embodiments, long ribs 112 project radially inward about 0.2 mm. In some embodiments, short ribs 113 project radially inward about 1 mm to about 3 mm (such as about 1 mm to about 3 mm or about 1.2 mm to about 1.5 mm). In some embodiments, short ribs 113 project radially inward about 1.2 mm.

Long ribs 112 may engage with corresponding recesses 210 on base 200. Long ribs 112 may slide within recesses 210 as delivery device is moved from a pre-delivery state (such as shown in FIG. 1) to a post-delivery state (such as shown in FIG. 2) such that injector barrel 100 and base 200 are prevented from rotating about axis 20 relative to each other. Short ribs 113 may be sized and positioned such that short ribs prevent lateral movement of vial 400 when vial 400 is disposed at least partially within injector barrel 100, as shown in FIGS. 4 and 5. Preventing lateral movement reduces the risk of breaking vial 400 when vial 400 is disposed within delivery device 10.

In some embodiments, vial 400 may be sized along with one or more components and/or features of the delivery device 10, such as interior volume 140 defined at least in part by inner tube 114, to deliver larger volumes of sterile medications, such as from about 0.2 mL to about 1 mL, which is significantly greater than the 0.1 mL delivery volume typically provided by other IN delivery devices or products. For example, currently commercially available IN delivery devices are only capable of one 100 μL (0.1 mL) dose and cannot accommodate or deliver larger dosage volumes. In addition, in some embodiments, delivery device 10 may be produced to be comparable in size (such as within 10-15% in total size or any single dimension, such as length or width) to currently available IN delivery devices or products and, thus, can be conveniently carried and/or used as needed.

Relating to the delivery of relatively large volume of medication intranasally, Clinical Study Report N002-CL-C incorporated by reference herein in its entirety and sponsored by Amphastar Pharmaceuticals, Inc., of Rancho Cucamonga, examines the safety of dosing volumes greater than or equal to 0.25 mL of IN medications in certain patient populations, such as in infants and young children between 0 and 3 years of age. The study indicates that the researchers found no evidence or safety concerns that IN dosing volumes greater than 0.25 mL pose undue risk or have diminished efficacy for children ≤3 years of age. Specifically, the study shows that the delivery of IN volume greater than 0.25 mL is safe and well tolerated for the general pediatrics or neonates/infants, respectively. Adverse events were minor and very rare, and occurrence of adverse events showed no association with age, or dosing volume. As a result of that discussed and shown by the study, delivery device 10 can be effectively used to deliver IN volume of sterile medication in relatively large volumes, such as from 0.2 mL to 1 mL per dosage.

FIGS. 10-15 illustrate various views of base 200, which may include flanges 202 (also referred to herein as "hooks" or "claw-type hooks") that extend outwardly from an outer surface of base 200. The region where flanges 202 protrude from base 200 may be referred to as a top portion. For example, within the top portion, in some embodiments, base 200 may include at least two flanges 202 (such as at least three flanges 202 or at least four (4) flanges 202). In some embodiments, the number of flanges 202 equals the number of slit openings 118. For example, in some embodiments, base 200 includes four flanges 202 and injector barrel 100 includes four slit openings 118. During assembly or actuation of the delivery device 10, flanges 202 may releasably engage with slit openings 118 to, for example, at least partially restrict axial movement of base 200 relative to injector barrel 100. Flanges 202 may be releasably engaged with slit openings 118 such that when flanges 202 disengage from slit openings 118, base 200 may move in the axial (such as vertical) direction relative to injector barrel 100. In some embodiments, flanges 202 are engaged with slit openings 118 when delivery device 10 is in the pre-delivery state, as shown in FIGS. 1 and 4. In this way, in some embodiments, flanges 202 may disengage from slit openings 118 in response to a force applied to delivery device 10. For example, flanges 202 may disengage from slit openings 118 in response to an upward force (such as in the direction of the arrow 50 of FIG. 7) applied to bottom surface 209 of base 200 or in response to a downward force (such as in the direction opposite of arrow 50) applied to injector barrel 100.

Flanges 202 may include a surface angled relative to a longitudinal dimension of base 200. Base 200 may include gaps 212 that define tabs 213. In some embodiments, flanges 202 extend out from the top of tabs 213. Base 200 may include recesses 204 oriented horizontally around the outer wall of base 200 below tabs 213. In some embodiments, recesses 204 reduce the initial break force of flanges 202. In some embodiments, recesses 204 may reduce gliding force necessary for successful delivery of the medication, such as by functioning with gaps 212 allowing tabs 213 to flex inward in response to a force (such as gliding force) applied to delivery device 10. For example, when an upward force is applied to base 200 or a downward force is applied to injector barrel 100, the angled surface of flanges 202 may contact an upper surface of slit openings 118 such that tabs 213 flexes inward toward axis 20. After sufficient force is applied, tabs 213 may flex enough to disengage flanges 202 from slit openings 118.

Base 200 may include lower flange 206 positioned at or near a bottom portion of base 200 and may extend around the entire base 200. The base 200 has an inner radius 261 extending from an outer surface of the base 200 to axis 21 and an outer radius 260 extending from axis 21 to the end of the base flange 206. As shown, inner radius 261 is smaller than outer radius 260 leaving a gap between the outer surface of the base wall 201 and the edge of the base flange 206. The outer radius 260 can be larger than radius 160 of injector barrel 100 such that axial movement is limited when the bottom of injector barrel 100 contacts lower flange 206 in the post-delivery state. For example, when an upward force is applied to base 200 or a downward force is applied to injector barrel 100 (this process referred to herein as "actuation" of the delivery device 10), base 200 may move relative to injector barrel 100 from a pre-delivery state as shown in FIGS. 1 and 4 to a post-delivery state as shown in FIGS. 2 and 5. Alternatively put, actuation of the delivery device 10 involves compression of base 200 toward barrel from the pre-delivery state to the post-delivery state, thereby forcing liquid 500 (also referred to as a medication solution) contained within vial 400 through cannula 700 and out of injector barrel 100.

Figure 11:
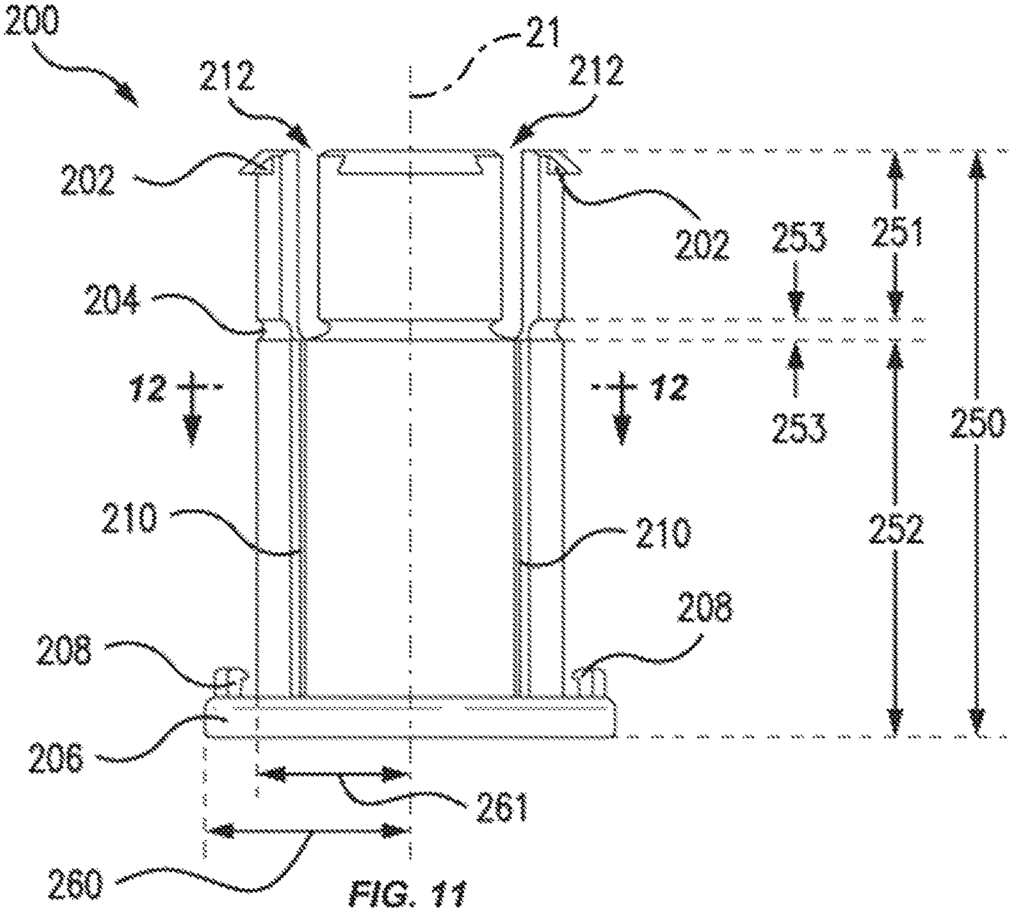
FIG. 11 shows a side view of the base of FIG. 10.

Base 200 (such as shown in FIG. 11) may include at least one latch 208 that projects upward from a top surface of lower flange 206. Base 200 may include openings 240 between latches 208 (such as a pair of latches or plurality of latches) and an outer surface of base 200. In this way, latches 208 may engage with bottom flange 120 of injector barrel 100 when delivery device 10 is in the post-delivery state. In some embodiments, latches 208 irreversibly engage with bottom flange 120 of injector barrel 100 when delivery device 10 is in the post-delivery state. In addition, flanges 202) and latches 208 are capable of producing tactile and/or audible feedback upon engagement with one or more of the slit openings 118 at separation from the pre-delivery state and at the post-delivery state.

Figure 12:
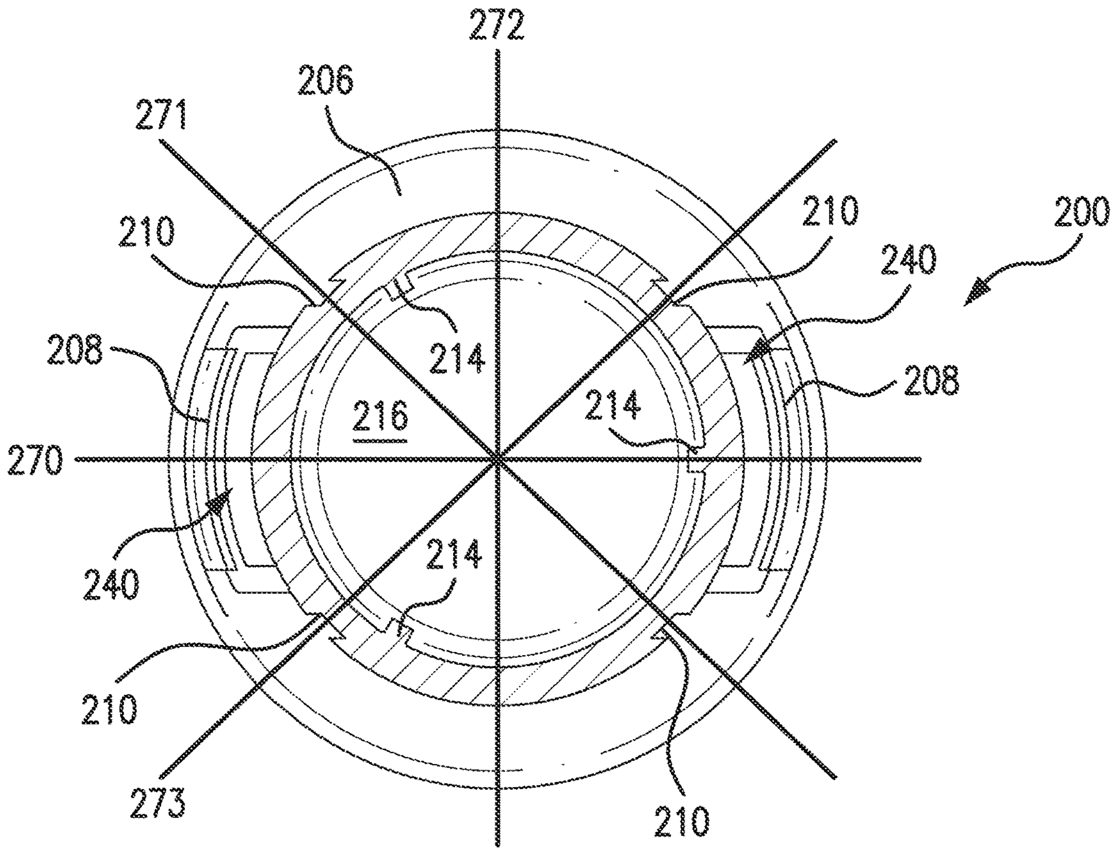
FIG. 12 shows a cross-section view of the base of FIG. 10 taken along an X-Z plane at line 12-12.
Figure 13:
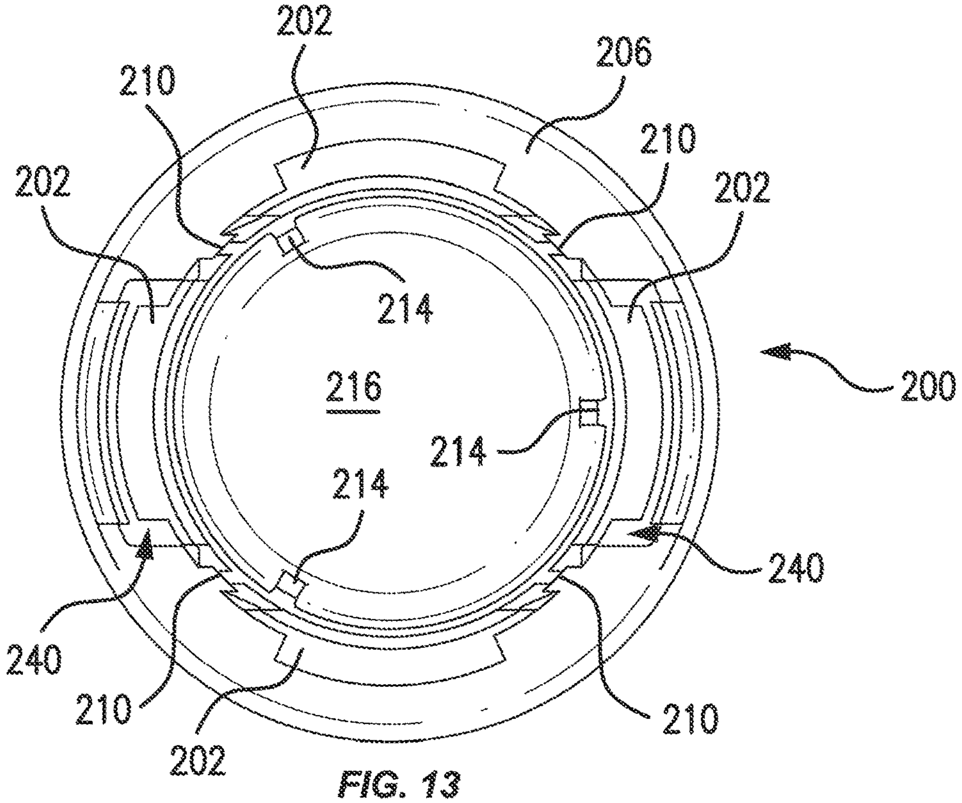
FIG. 13 shows a top-down view of the base of FIG. 10.
Figure 15:
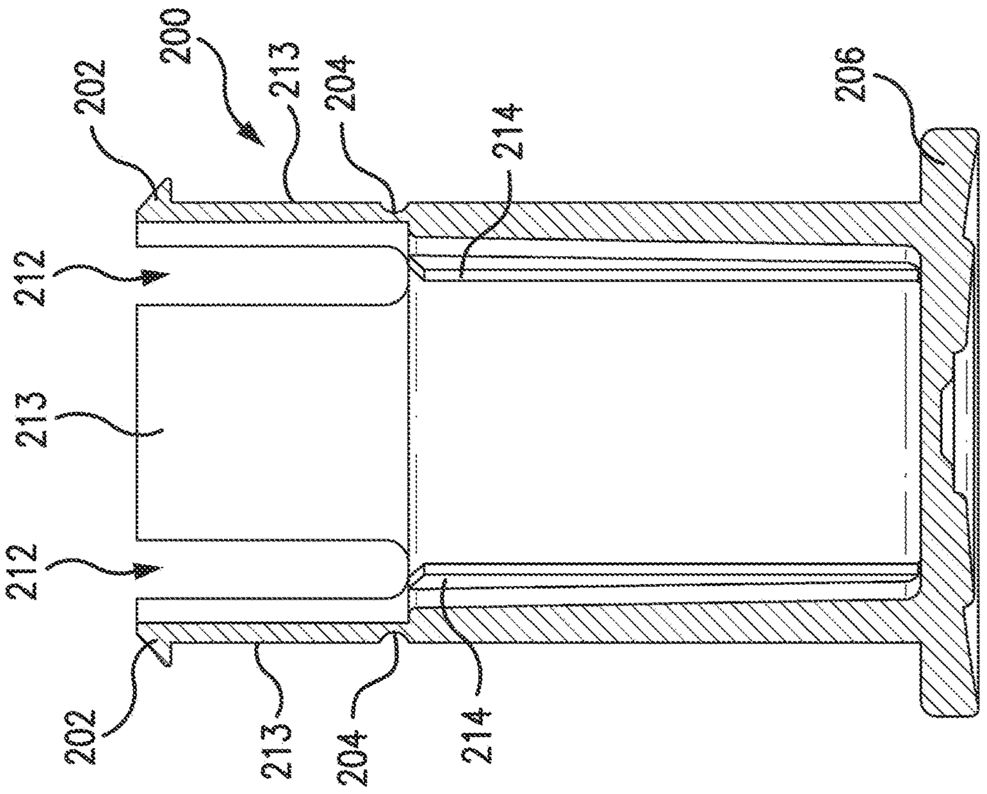
FIG. 15 shows a cross-section of the base of FIG. 10 taken along line 15-15.
Figure 14:
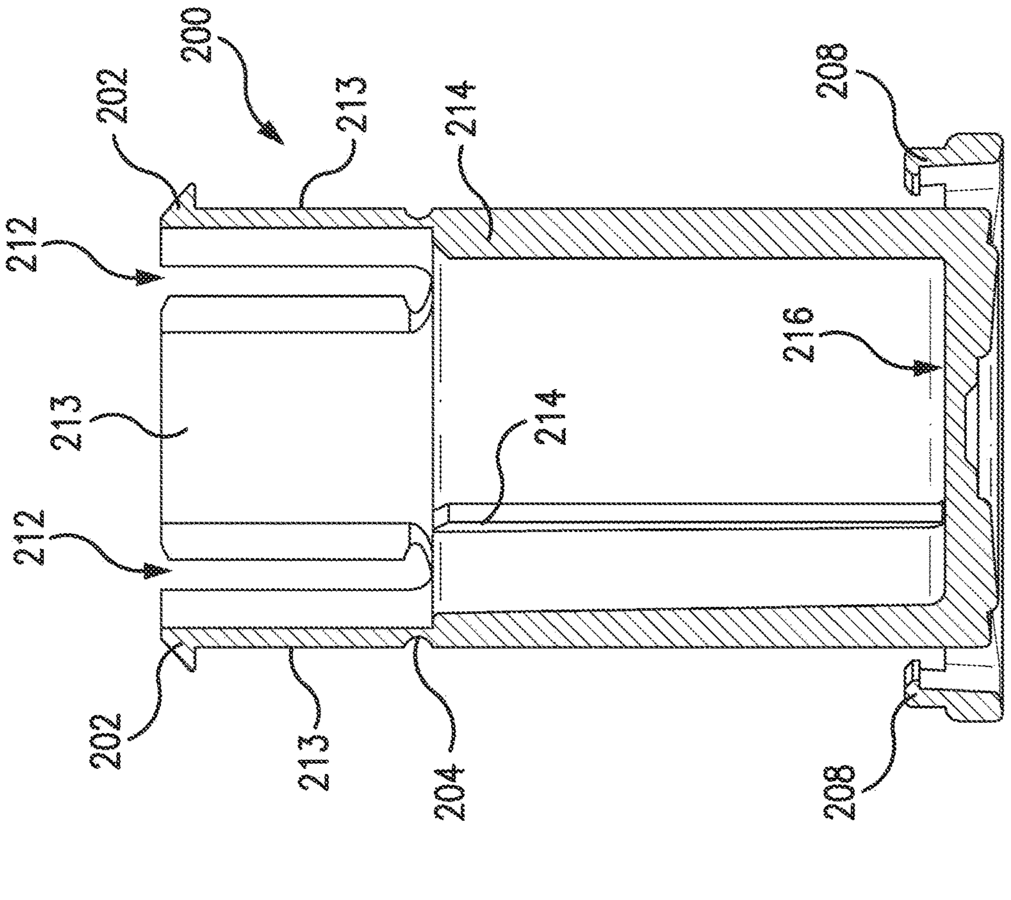
FIG. 14 shows a cross-section of the base of FIG. 10 taken along line 14-14.

Base 200 may include at least one recess 210 that forms a groove in the outer surface of base 200. In some embodiments, recesses 210 each have a longitudinal dimension extending in the direction of axis 20. In this way, recesses 210 may releasably engage with long ribs 112 on injector barrel 100 such that base 200 is restricted from rotating relative to injector barrel 100. Base 200 may include at least two recesses 210 (such as at least three recesses 210 or at least four recesses 210). In some embodiments, the number of recesses 210 equals the number of long ribs 112. For example, in some embodiments, base 200 includes four recesses 210 and injector barrel 100 includes four long ribs 112. As shown in FIG. 12, recesses 210 may be positioned at an angle of 45 degrees relative to the X-axis 270 and Z-axis 272 along lines 271 and 273.

Base 200 may include at least one base rib 214 that projects radially inward from an inner surface of base 200 into inner volume 216 of base 200. In some embodiments, base 200 includes three base ribs 214, as shown in FIGS. 12-15. In some embodiments, base 200 includes three base ribs 214 spaced evenly around base 200. Base ribs 214 may be sized and positioned such that base ribs 214 prevent lateral movement of vial 400 when vial 400 is disposed at least partially within base 200, as shown in FIGS. 4 and 5.

Base 200 may have a geometry and dimensions such that it can cooperate with injector barrel 100 as delivery device 10 moves from a pre-delivery state to a post-delivery state. For example, as shown in FIG. 11, base 200 may have an overall height 250, tabs 213 may have a height 251, lower portion of base 200 may have a height 252, and recesses 204 may each have a height 253. In some embodiments, the sum of heights 251, 252, and 253 equals overall height 250 of base 200. Overall height 250 may be about 20 mm to about 35 mm (such as about 25 mm to about 30 mm). In some embodiments, overall height 250 is about 27 mm. Height 251 may be large enough such that tabs 213 may flex, but not so large that tabs 213 will break. For example, height 251 may be about 5 mm to about 10 mm (such as about 7 mm to about 8 mm). In some embodiments, height 251 is about 8 mm. In some embodiments, height 251 is about 25% to about 30% of overall height 250. Height 252 may be about 15 mm to about 25 mm (such as about 18 mm to about 20 mm). In some embodiments, height 252 is about 18.5 mm. Height 253 may be about 0.5 mm to about 1.5 mm (such as about 0.8 mm to about 1 mm). In some embodiments, height 253 is about 0.9 mm.

Delivery device 10 may include vial 400 (as shown in FIG. 3) disposed (such as inserted) within delivery device 10. Vial 400 may be made of various materials, including glass, acrylic, or polycarbonate. Such materials may be rigid, yet also resistant to breakage upon application of force as needed for actuation of delivery device 10. In some embodiments, vial 400 is a glass vial. In some embodiments, vial 400 is disposed at least partially in injector barrel 100 and at least partially in base 200. In some embodiments, vial 400 is removable and replaceable. In some embodiments, vial 400 is not replaceable and delivery device 10 is a single-use device. In some embodiments, vial 400 is coupled to base 200 using an adhesive (such as a glue). In some embodiments, the adhesive is a UV-curable adhesive. In addition, vial 400 may have a capacity of about 1 $cm^3$ to about 5 $cm^3$ (such as about 2 $cm^3$ to about 3 $cm^3$). In some embodiments, vial 400 has a capacity of about 3 $cm^3$.

Delivery device 10 may include stopper 300 disposed within vial 400. In some embodiments, stopper 300 is disposed within vial 400 and coupled to vial 400 by an interference fit (also referred to as a "pressed-fit"). In some embodiments, at least a portion of stopper 300 is disposed within an interior volume of inner tube 114. When vial 400 is disposed within delivery device 10, stopper 300 and at least a portion of inner tube 114 may be disposed within vial 400. When delivery device 10 is in the pre-delivery state, as shown in FIG. 4A, vial 400 may include an interior volume 410 defined in part by vial 400 and in part by stopper 300. Stopper 300 may be inserted into vial 400 by a vacuum stoppering process. For example, the vacuum stoppering process may pull vacuum in the head space of vial 400 before inserting stopper 300. This allows for stopper 300 to glide down by vacuum and results in small head space. In addition, the vacuum stoppering process may allow stopper 300 to later diametrically expand to compress against vial 400 and thereby a form a gas-phase impermeable seal with an internal surface of vial 400.

Vial 400 may hold a liquid 500 within interior volume 410 of vial 400. Liquid 500 may be a sterile medication for delivery to a patient using delivery device 10. For example, in some embodiments, liquid 500 includes naloxone. In some embodiments, liquid 500 includes naloxone at a concentration of about 10 mg/mL to about 50 mg/mL (such as about 10 mg/mL to about 20 mg/mL or about 30 mg/mL to about 50 mg/mL). In some embodiments, liquid 500 includes naloxone at a concentration of about 16 mg/mL or at a concentration of about 40 mg/mL. In some embodiments, liquid 500 includes naloxone that may be aerosolized and administered intranasally using delivery device 10.

Referring to FIG. 4A, delivery device 10 may include cannula 700 in fluid communication with vial 400. In some embodiments, cannula 700 is a needle. In some embodiments, cannula 700 is centered by flange 106. In some embodiments, cannula 700 is coupled to injector barrel 100 by inserting an adhesive into the inner space defined by upward projection 102. In some embodiments, cannula 700 is coupled to injector barrel 100 using an adhesive (such as a glue). Various adhesives may be used, including epoxy adhesive, polyurethane adhesive, cyanoacrylates, LED-curable adhesives, or UV-curable adhesives. In some embodiments, the adhesive is a UV-curable adhesive. Cannula 700 may include a sharp bottom end such that when delivery device 10 moves from the pre-delivery state as shown in FIG. 4A to the post-delivery state shown in FIG. 5, cannula 700 pierces stopper 300 to create a flow path from interior volume 410 to an outlet of delivery device 10. Alternatively put, cannula 700 may accordingly bisect stopper 300. After cannula 700 pierces stopper 300, a flow path for liquid 500 may be formed from interior volume 410, through cannula 700 and nozzle 800, to outlet 910.

In some embodiments, when delivery device 10 is fitted with cannula 700, delivery device 10 may be used to deliver a medication by sliding base 200 relative to injector barrel 100. In some embodiments, base 200 slides in response to a force applied in the direction of arrow 50 (such as shown in FIG. 4A). As base 200 slides, base 200 pushes vial 400 so that vial 400 slides in the direction of arrow 50. As vial 400 slides, vial 400 pushes stopper 300.

Delivery device 10 may include guide 600 (also referred to as a "center guide") disposed within inner tube 114. Guide 600 may include a central opening capable of accommodating cannula 700 and center cannula 700 within inner tube 114 and vial 400. Guide 600 may include a chamfer that guides the cannula 700 to the opening and into a centered position within delivery device 10. Cannula 700 may pass through the central opening of guide 600, and guide 600 may prevent lateral movement of cannula 700.

Delivery device 10 may deliver liquid 500 to a patient for IN administration of liquid 500. For example, as delivery device 10 moves from the pre-delivery state to the post-delivery state, liquid 500 may be expelled through the flow path described above. In some embodiments, liquid 500 is dispensed as an aerosol. Nozzle 800 and cap 900 may aerosolize liquid 500 as it is dispensed from delivery device 10. For example, nozzle 800 may include openings of a suitable size to produce an aerosol as liquid 500 is dispensed and cap 900 may include outlet 910 through which the aerosol is dispensed. In some embodiments, liquid 500 is dispensed as an aerosol having a droplet size of about 15 μm to about 125 μm (such as about 15 μm to about 35 μm, about 35 μm to about 65 μm, or about 80 μm to about 125 μm). In some embodiments, liquid 500 is aerosolized and dispensed with a spray pattern appropriate for IN administration. As used herein, "spray pattern" is the measurement of the cross-sectional uniformity of the spray plume. The spray pattern having an oval shape, with no axis greater than 40 mm. Liquid 500 may be aerosolized and administered at a pressure of about 20 N to about 40 N.

Delivery device 10 may provide an indication when used to indicate that a full dose of a medication (such as liquid 500) has been dispensed. For example, the noise may be caused by base 200 touching injector barrel 100 after a full dose of a sterile medication (such as liquid 500) has been dispensed. In some embodiments, the indicator is an audible noise (such as a clicking sound). In some embodiments, the audible noise is produced when delivery device 10 reaches the post-delivery state. In addition, in some embodiments, injector barrel 100 has a first color (such as white) and base 200 has a second color (such as green) dissimilar to the first color. Accordingly, dissimilarity in coloration between injector barrel 100 and base 200 facilitates convenient identification of the pre-delivery position and the post-delivery position.

The various components of delivery device 10 may be made using any suitable method. For example, in some embodiments, injector barrel 100, base 200, guide 600, nozzle 800, and cap 900 may be made by injection molding. In some embodiments, injector barrel 100, base 200, guide 600, nozzle 800, and cap 900 are all injection molded components. In some embodiments, delivery device 10 includes a barrel cap (not shown in the figures) that may be inserted into the bottom opening of injector barrel 100. The barrel cap may include an upward projection that fits within inner tube 114 to ensure that inner tube 114 remains centered until the entire delivery device 10 is assembled. In some embodiments, barrel cap is temporarily used during assembly and is removed before the entire delivery device 10 is assembled. In some embodiments, the barrel cap may fit within inner tube 114 by interference fit within inner tube 114 such that inner tube 114 remains centered and does not move laterally. The barrel cap may also include outward projections for insertion into slit openings 118.

The various components of delivery device 10 may be made of any suitable material. For example, the components may be made of any suitable thermoplastic material including, for example, polypropylene, polycarbonate, or polyethylene and/or the like. In some embodiments, injector barrel 100, base 200, guide 600, and cap 900 are all made of polypropylene. In some embodiments, nozzle 800 is made of polycarbonate.

Delivery device 10 may be used to administer liquid 500. Initially, delivery device may be placed proximate to a patient's nostril such that cap 900 is inserted into a user's nostril. To begin administering liquid 500, a user may apply force to delivery device 10 so that flanges 202 disengage from slit openings 118 of injector barrel 100. In some embodiments, downward force is applied to injector barrel 100 (such as using finger flanges 116) such that injector barrel 100 moves downward relative to base 200 from the pre-delivery state to the post-delivery state. In some embodiments, upward force is applied to base 200 (such as by pressing bottom surface 209 of base 200) such that base 200 moves upward relative to injector barrel 100.

As described above, recesses 210 slide along long ribs 112 as base 200 moves relative to injector barrel 100. Vial 400 may move with base 200. Stopper 300 may also move with base 200. As stopper 300 moves upwards within inner tube 114, stopper 300 may contact the sharp bottom end of cannula 700 such that cannula 700 pierces stopper 300 as base 200 and stopper 300 move upward. When cannula 700 pierces stopper 300, the pressure within interior volume 410 is released, which forces liquid 500 out of vial 400. After piercing, base 200 continues to move relative to injector barrel 100, forcing liquid 500 out of vial 400, until base 200 reaches the post-delivery state. Once reaching the post-delivery state, latches 208 on base 200 engage with bottom flange 120 of injector barrel 100. In some embodiments, latches 208 irreversibly engage with bottom flange 120. In some embodiments, delivery device 10 produces an audible sound when latches 208 engage with bottom flange 120. Although the movement of components of delivery device 10 are described with respect to base 200 moving relative to injector barrel 100, it is to be understood that injector barrel 100 could move with respect to base 200, and delivery device 10 would function in the same manner.

Figure 16:
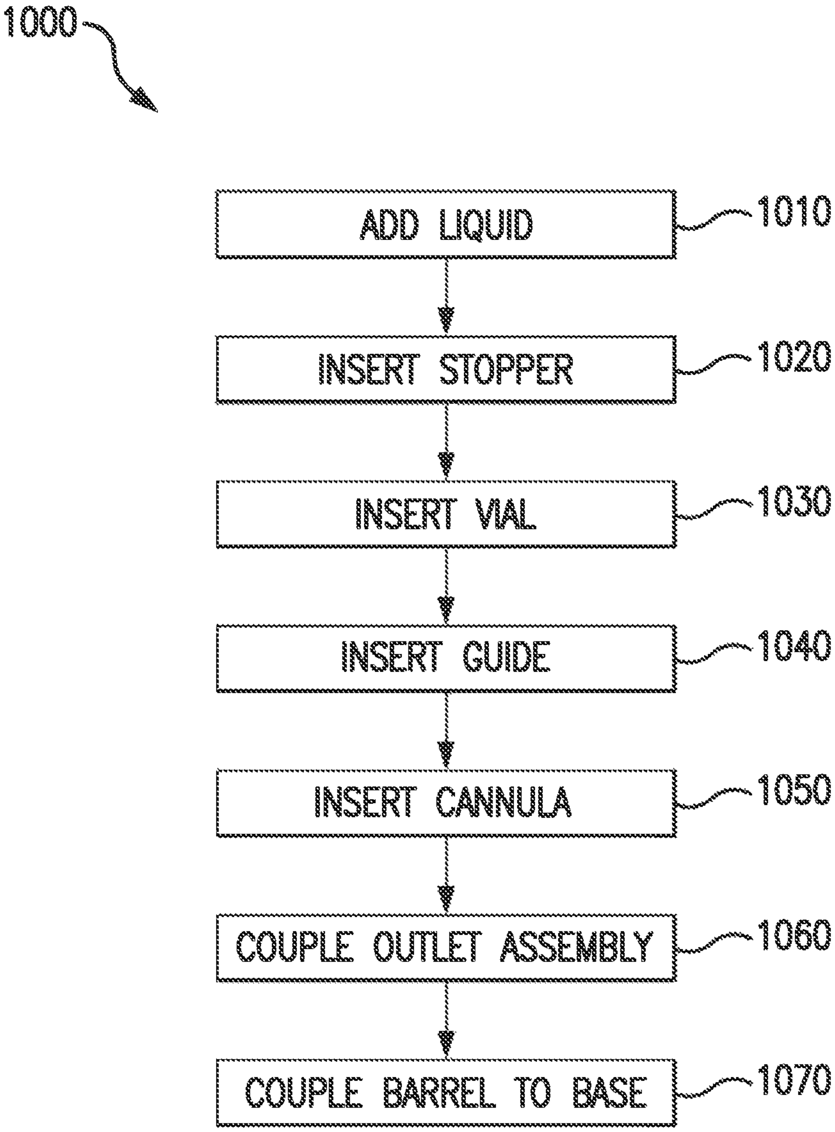
FIG. 16 shows steps of assembling a delivery device according to some embodiments.

Delivery device 10 may be assembled according to assembly method 1000 shown in FIG. 16. Unless otherwise noted, it is to be understood that the assembly of the order of the steps of assembly method 1000 may be varied. At (1010), liquid 500 may be added to vial 400. In some embodiments, liquid 500 is a medication. At (1020), stopper 300 may be inserted into vial 400. In some embodiments, stopper 300 is inserted using a vacuum stoppering process.

At (1030), at least a portion of vial 400 may be inserted into an interior volume of base 200. In some embodiments, vial 400 is inserted into an interior volume of base 200 after liquid 500 has been added to vial 400. In some embodiments, vial 400 is coupled to base 200 at step 1030. In some embodiments, vial 400 is coupled to base 200 by interference fit. In some embodiments, vial 400 is coupled to base 200 using an adhesive (such as a glue).

At (1040), guide 600 may be inserted into inner tube 114. In some embodiments, guide 600 is inserted before cannula 700 is inserted at (1050).

At (1050), cannula 700 may be inserted into injector barrel 100. In some embodiments, cannula 700 is coupled to injector barrel 100 at (1050). In some embodiments, cannula 700 is coupled to injector barrel 100 by an adhesive (such as a glue). In some embodiments, as illustrated in FIGS. 4 and 5, cannula 700 extends through an opening at the center of guide 600. In some embodiments, cannula 700 is centered by flange 106. As described above, cannula 700 may be coupled to injector barrel 100 by inserting an adhesive into the inner space defined by upward projection 102. In some embodiments, (1050) includes adding an adhesive (such as a glue) to the inner space defined by upward projection 102 after cannula 700 is inserted. In some embodiments, the adhesive is a UV-curable adhesive, and (1050) includes curing the UV-curable adhesive. At (1060), the outlet assembly may be coupled to injector barrel 100. In some embodiments, nozzle 800 is inserted into cap 900 before the outlet assembly is coupled to injector barrel 100. In some embodiments, outlet cap 900 is coupled to injector barrel 100 by a spin weld process. By coupling nozzle 800 to a top end of injector barrel 100 such that cannula 700 is covered by nozzle 800. Then cap 900 may be coupled to both nozzle 800 and injector barrel 100. In some embodiments, nozzle 800 is coupled to injector barrel 100 by an interference fit. In some embodiments, cap 900 is coupled to nozzle 800 and injector barrel 100 by an interference fit.

At step (1070), injector barrel 100 may be coupled to base 200. In some embodiments, injector barrel 100 is placed over base 200 and slid down relative to base 200 until flanges 202 on base 200 engage with slit openings 118 of injector barrel 100. In some embodiments, base 200 is placed into injector barrel 100 and slid up relative to injector barrel 100 until flanges 202 on base 200 engage with slit openings 118 of injector barrel 100.

In some embodiments, method 1000 includes each of (1010) through (1070). In some embodiments, vial 400 is pre-filled and pre-stoppered and method 1000 includes each of (1030) through (1070).

Referring to FIG. 17, a table is shown comparing sample data measured for seal rings 301, 302, and 303 of stopper 300 shown in FIG. 4C. Multiple samples were taken using an Optical Gaging Products (OGP) SmartScope® Flash™ 500 and numbered incrementally from "1" through "5." Of note, measurements for seal ring 301 is denoted as "top rib," seal ring 302 is denoted as "middle ring," and seal ring 303 is denoted as "bottom rib." In addition, "Location 1" and "Location 2" are two measurements taken on the same rib (or seal ring). "Sub-Ave" was calculated by taken the average of only the measurement of "Location 1" and "Location 2" for that sample number for that particular seal ring. Further, thicknesses were reported for when stopper 300 is fully expanded within vial 400 forming a gas-phase impermeable seal with an internal circumferential surface of vial 400. Consequently, as shown by the measurement values in table of FIG. 17, each seal ring of stopper 300 has a geometry configured to form a gas-phase impermeable seal with an internal circumferential surface of vial 400 and is also significantly larger than comparable features in the Aptar® Unidose Delivery System, another type of IN delivery device comparatively compared to the disclosed device.

As used herein, the terms "upper" and "lower," "top" and "bottom," and "inner" and "outer," and the like are intended to assist in understanding of embodiments of the disclosure with reference to the accompanying drawings with respect to the orientation of the beverage closure as shown, and are not intended to be limiting to the scope of the disclosure or to limit the disclosure scope to the embodiments depicted in the Figures. The directional terms are used for convenience of description, and it is understood that the delivery device may be positioned in any of various orientations.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An intranasal delivery gas-phase impermeable device for delivery between about 0.2 mL and about 1.0 mL of a medication solution in a single actuation, the intranasal delivery gas-phase impermeable device comprising:

a) an injector barrel comprising:

an external cylindrical tube having a plurality of slit openings disposed circumferentially along a bottom of the external tube of the injector barrel;

an inner cylindrical tube inside the external tube, the inner cylindrical tube extending lengthwise from an upper portion to approximately the plurality of slit openings of the external cylindrical tube;

a centering guide positioned lengthwise within the inner cylindrical tube; and a cannula in fluid communication with the medication solution and secured in position by the centering guide;

b) a vial configured to couple with the injector barrel, the vial comprising:

a pliable rubber stopper including a plurality of seal rings, each seal ring having a geometry configured to form a gas-phase impermeable seal with an internal surface of the vial, wherein the cannula bisects the pliable rubber stopper; and c) a base configured to reversibly engage with one or more of the slit openings of the injector barrel during actuation of the intranasal delivery gas-phase impermeable device.

2. The intranasal delivery gas-phase impermeable device of claim 1, wherein the external tube, the inner tube, the centering guide, and the cannula of the injector barrel are homocentric.

3. The intranasal delivery gas-phase impermeable device of claim 1, wherein the injector barrel further comprises a tip configured to deliver medication into a nostril of a patient and further configured to form an interference fit within a circumference of the nostril of the patient, wherein a length of the tip is not more than 25 mm.

4. The intranasal delivery gas-phase impermeable device of claim 1, wherein a diameter of the external tube of the injector barrel is larger than a nostril of a patient.

5. The intranasal delivery gas-phase impermeable device of claim 1, wherein the external cylindrical tube of the injector barrel further comprises a pair of finger flanges extending laterally away from the injector barrel, each finger flange positioned diametrically opposite to each other, and wherein each finger flange is configured to support a user's finger.

6. The intranasal delivery gas-phase impermeable device of claim 1, wherein the external tube comprises a plurality of ribs, wherein each rib is disposed lengthwise on an inner surface of the external tube, wherein the plurality of ribs are configured to (i) guide the base in a fixed clockwise or counterclockwise position within the injector barrel and (ii) hold the vial in a radially fixed position.

7. The intranasal delivery gas-phase impermeable device of claim 1, wherein the vial comprises glass or plastic, further wherein the vial is configured as a cylinder-shaped vial with a flat bottom, a cylinder-shaped tube with a non-flat bottom, or a cartridge tube.

8. The intranasal delivery gas-phase impermeable device of claim 1, wherein the medication solution comprises a sterile medication solution or a non-sterile medication solution.

9. The intranasal delivery gas-phase impermeable device of claim 1, wherein the vial is configured to store the medication solution between the pliable rubber stopper and a bottom section of the vial.

10. The intranasal delivery gas-phase impermeable device of claim 1, wherein the medication solution comprises a true solution, a suspension, or an emulsion.

11. The intranasal delivery gas-phase impermeable device of claim 1, wherein the medication solution comprises one or more active pharmaceutical ingredients (APIs) selected from epinephrine ($C_9H_{13}NO_3$), ketorolac ($C_{15}H_{13}NO_3$), naloxone ($C_{19}H_{21}NO_4$), midazolam ($C_{18}H_{13}ClFN_3$), sildenafil ($C_{22}H_{30}N_6O_4S$), tadalafil ($C_{22}H_{19}N_3O_4$), phytonadione ($C_{31}H_{46}O_2$), insulin aspart ($C_{256}H_{381}N_{65}O_{79}S_6$), nitroglycerin ($C_3H_5N_3O_9$), teriparatide ($C_{181}H_{291}N_{55}O_{51}S_2$), or combinations thereof.

12. The intranasal delivery gas-phase impermeable device of claim 1, wherein the pliable rubber stopper forms a plurality of seals in circumferentially full contact between the inner surface of the vial and the rubber stopper, wherein each seal has a thickness of at least about 1 mm or more such that ingress of gaseous substance is effectively limited at a temperature between about 25° C. to about 40° C. and at a relative humidity between about 60% to about 75%.

13. The intranasal delivery gas-phase impermeable device of claim 1, wherein the gas-phase impermeable seal is configured to prevent fluid exchange, microorganism and/or particulate exchange between the medication solution contained within the vial and one or more other regions within the vial, such that undesirable contamination of the medication solution is prevented.

14. The intranasal delivery gas-phase impermeable device of claim 1, wherein the gas-phase impermeable seal prevents contact between a gaseous substance contained within the vial and the medication solution.

15. The intranasal delivery gas-phase impermeable device of claim 14, wherein the gaseous substance is oxygen.

16. The intranasal delivery gas-phase impermeable device of claim 1, wherein the base comprises a top portion and a bottom portion positioned opposite to the top portion, the base further comprising:

(i) a plurality of hooks located at the top portion configured to initially engage with one or more of the plurality of slit openings of the injector barrel at a pre-delivery position; and (ii) a plurality of latches extending from the base at the bottom portion configured to mechanically engage with the plurality of slit openings of the injector barrel at a post-delivery position.

17. The intranasal delivery gas-phase impermeable device of claim 16, wherein the plurality of hooks and the plurality of latches in the base are configured to produce tactile and/or audible feedback upon engagement with one or more of the plurality of slit openings in the pre-delivery position and/or at the post-delivery position.

18. The intranasal delivery gas-phase impermeable device of claim 1, wherein the injector barrel comprises a first color and the base comprises a second color, wherein the first color and the second color are different, such a dissimilarity in coloration between the injector barrel and the base facilitates convenient identification of a pre-delivery position and a post-delivery position.

19. The intranasal delivery gas-phase impermeable device of claim 1, wherein actuation of the intranasal delivery gas-phase impermeable device involves compression of the base toward the injector barrel from a pre-delivery position to a post-delivery position thereby forcing the medication solution contained within the vial through the cannula and out of an intranasal tip of the injector barrel.

20. The intranasal delivery gas-phase impermeable device of claim 1, wherein actuation of the intranasal delivery gas-phase impermeable device disperses the medication solution into a nasal cavity of a patient who is in one or more of an incapacitated position, an unconscious position, or lying in a supine position.

21. An intranasal delivery device for delivering a medication solution, the intranasal delivery device comprising:

a) an injector barrel comprising:

an external tube with a plurality of transverse slit openings disposed circumferentially along the external tube;

an inner tube that is homocentric with the external tube;

a centering guide positioned lengthwise within the inner tube of the injector barrel; and a cannula in fluid communication with the medication solution secured in position by centrally bisecting the center guide;

b) a vial configured to couple with the injector barrel, the vial comprising:

a vial having a base section, the vial comprising a glass material or a plastic material;

a pliable rubber stopper positioned above the base section of the vial, the pliable rubber stopper comprising a plurality of seal rings, each seal ring having a geometry configured to form a gas-phase impermeable seal; wherein the cannula is configured to centrally bisect the pliable rubber stopper, wherein the pliable rubber stopper is configured to contact inside the inner tube when the vial is coupled to the injector barrel; and a liquid medication disposed within the vial having volume of between about 0.2 mL and about 1.0 mL; and c) a base having a top portion and a bottom portion positioned opposite to the top portion, the base configured to engage with one or more of the plurality of transverse slit openings of the injector barrel during actuation of the intranasal delivery device, the base including:

a plurality of hooks located at the top portion configured to engage with one or more of the plurality of transverse slit openings of the injector barrel at a pre-delivery position; and a plurality of latches extending from the base at the bottom portion configured to engage with one or more of the transverse slit openings at a post-delivery position.

* * * * *